(12) United States Patent
Ahmad et al.

(10) Patent No.: US 10,829,496 B2
(45) Date of Patent: Nov. 10, 2020

(54) THIENOPYRIDINES AND BENZOTHIOPHENES USEFUL AS IRAK4 INHIBITORS

(71) Applicant: BRISTOL-MYERS SQUIBB COMPANY, Princeton, NJ (US)

(72) Inventors: Saleem Ahmad, Wall, NJ (US); Ling Li, Pennington, NJ (US); Lidet A. Negash, Plainsboro, NJ (US); John Hynes, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/612,478

(22) PCT Filed: May 10, 2018

(86) PCT No.: PCT/US2018/031945
§ 371 (c)(1),
(2) Date: Nov. 11, 2019

(87) PCT Pub. No.: WO2018/209012
PCT Pub. Date: Nov. 15, 2018

(65) Prior Publication Data
US 2020/0062777 A1    Feb. 27, 2020

Related U.S. Application Data

(60) Provisional application No. 62/504,956, filed on May 11, 2017.

(51) Int. Cl.
*C07D 495/04*    (2006.01)
*C07D 409/12*    (2006.01)

(52) U.S. Cl.
CPC ......... *C07D 495/04* (2013.01); *C07D 409/12* (2013.01)

(58) Field of Classification Search
CPC ............................ C07D 495/04; C07D 409/12
USPC ......................................................... 514/301
See application file for complete search history.

(56) References Cited

U.S. PATENT DOCUMENTS

| | | | | |
|---|---|---|---|---|
| 4,877,793 | A | * 10/1989 | Davies | A61P 9/00 514/301 |
| 8,575,153 | B2 | 11/2013 | Kitamura et al. | |
| 8,586,751 | B2 | 11/2013 | De Lucca et al. | |
| 9,663,467 | B2 | 5/2017 | Moslin et al. | |
| 2005/0272753 | A1 | 12/2005 | Nagashima et al. | |
| 2006/0148800 | A1 | 7/2006 | Stadtmueller et al. | |
| 2009/0082329 | A1 | 3/2009 | Halley et al. | |
| 2011/0230467 | A1 | 9/2011 | Shirakami et al. | |

FOREIGN PATENT DOCUMENTS

| | | |
|---|---|---|
| EP | 2532656 A1 | 12/2012 |
| GB | 2388596 | 11/2003 |

(Continued)

OTHER PUBLICATIONS

Annual Reports in Medicinal Chemistry, vol. 49, pp. 117-133.
(Continued)

*Primary Examiner* — Niloofar Rahmani
(74) *Attorney, Agent, or Firm* — Gary Greenblatt

(57) ABSTRACT

Disclosed are compounds of Formula (I) or a salt or prodrug thereof, wherein: X is $CR_4$ or N; Y is $CR_5$ or N; provided that only one of X and Y is N; (R1) is: or; wherein $R_1$, $R_{1a}$, $R_{1b}$, $R_{1c}$, $R_2$, and $R_3$ are define herein. Also disclosed are methods of using such compounds as modulators of IRAK4, and pharmaceutical compositions comprising such compounds. These compounds are useful in treating, preventing, or slowing inflammatory and autoimmune diseases, or in the treatment of cancer.

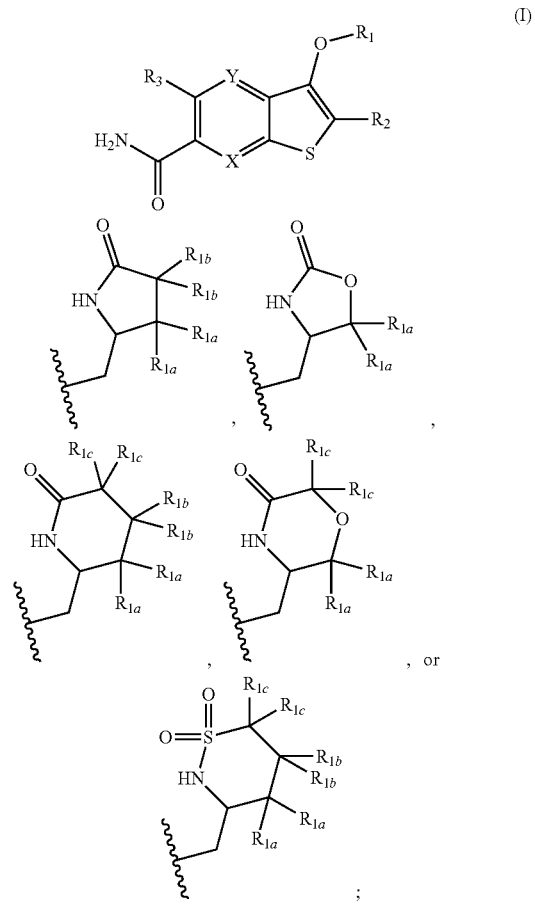

21 Claims, No Drawings

(56) References Cited

FOREIGN PATENT DOCUMENTS

| WO | WO02102800 A1 | 12/2002 |
|---|---|---|
| WO | WO03013523 A1 | 2/2003 |
| WO | WO2004065378 A1 | 8/2004 |
| WO | WO2005007646 A1 | 1/2005 |
| WO | WO2005075468 A2 | 8/2005 |
| WO | 06098962 A1 | 9/2006 |
| WO | 08063202 A2 | 5/2008 |
| WO | WO2008148889 A1 | 12/2008 |
| WO | WO2009046416 A1 | 4/2009 |
| WO | 11028995 A1 | 3/2011 |
| WO | 11029001 | 3/2011 |
| WO | WO2011053701 A1 | 5/2011 |
| WO | WO2012149567 A1 | 11/2012 |
| WO | WO2013106612 A1 | 7/2013 |
| WO | WO2013106614 A1 | 7/2013 |
| WO | WO2013106641 A1 | 7/2013 |
| WO | WO2014074657 A1 | 5/2014 |
| WO | WO2014074660 A1 | 5/2014 |
| WO | WO2014074675 A1 | 5/2014 |
| WO | WO2016144844 A1 | 9/2016 |
| WO | WO2016144849 A1 | 9/2016 |
| WO | WO2016210034 A1 | 12/2016 |
| WO | WO2016210037 A1 | 12/2016 |

OTHER PUBLICATIONS

Buckley, IRAK-4 inhibitors. Part 1: A series of amides, Apr. 26, 2008, 3211-3214, 18, Bioorganic & Medicinal Chemistry Letters.

Buckley_etal_Bioorganic_Medicinal_Chem_Letters_vol. 18_No. 11_2008_3291.

Buckley_etal_Bioorganic_Medicinal_Chem_Letters_vol. 18_No. 11_2008_3656.

Cario, Elke, "Toll-like Receptors in Inflammatory Bowel Diseases: A Decade Later", Inflamm Bowel Dis, 2010, vol. 16, pp. 1583-1597.

Chung, Yeonseok, et al., "Critical Regulation of Early Th17 Cell Differentiation by Interleukin-1 Signaling", Immunity, 2009, vol. 30, pp. 576-587.

Couillin, Isabelle, et al., "IL-1R1/MyD88 Signaling Is Critical for Elastase-Induced Lung Inflammation and Emphysema 1" The Journal of Immunology, 2009, vol. 183, pp. 8195-8202.

Dinarello, Charles A., "A clinical perspective of IL-1b as the gatekeeper of inflammation", Eur. J. Immunol., 2011, vol. 41, pp. 1203-1217.

Flannery, Sinead, et al., "The interleukin-1 receptor-associated kinases: Critical regulators of innate immune signalling", Biochemical Pharmacology, 2010, vol. 80, pp. 1981-1991.

Fraczek, Jerzy, et al., "The Kinase Activity of IL-1 Receptor-associated Kinase 4 Is Required for Interleukin-1 Receptor/Toll-like Receptor-induced TAK1-dependent NFKB Activation", The Journal of Biological Chemistry, 2008, vol. 283, No. 46, pp. 31697-31705.

Goldstein, Daniel R., "Review Article Targeting Toll-Like Receptors for Treatment of SLE", J Heart Lung Transplant, 2005, vol. 24, pp. 1721-1729.

Horton, Christopher G., "Review Article Targeting Toll-Like Receptors for Treatment of SLE", Hindawi Publishing Corporation, Mediators of Inflammation, 2010, vol. 2010, Article ID 498980, pp. 1-9.

International Searching Authority, dated 2018, International Application No. PCT/US2018/031945, 12 pgs.

Kawagoe, Tatsukata, et al., "Essential role of IRAK-4 protein and its kinase activity in Toll-like receptor-mediated immune responses but not in TCR signaling", The Journal of Experimental Medicine, 2007, vol. 204, No. 5, pp. 1013-1024.

Kawai, Taro, et al., "The role of pattern-recognition receptors in innate immunity: update on Toll-like receptors", Nature Immunology, 2010, vol. 11, No. 5, pp. 373-384.

Keogh, Brian, et al., "Toll-like receptors as targets for immune disorders", Trends in Pharmacological Sciences, 2011, vol. 32, No. 7, pp. 435-442.

Kim, Tae Whan, et al., "The Critical Role of IL-1 Receptor-Associated Kinase 4-Mediated NF-kB Activation in Modified Low-Density Lipoprotein-Induced Inflammatory Gene Expression and Atherosclerosis", The Journal of Immunology, 2011, vol. 186, pp. 2871-2880.

Kitazawa, Masashi, et al., "Blocking IL-1 Signaling Rescues Cognition, Attenuates Tau Pathology, and Restores Neuronal b-Catenin Pathway Function in an Alzheimer's Disease Model", The Journal of Immunology, 2011, vol. 187, pp. 6539-6549.

Koziczak-Holbro, Magdalena, et al., "IRAK-4 Kinase Activity Is Required for Interleukin-1 (IL-1) Receptor- and Toll-like Receptor 7-mediated Signaling and Gene Expression", The Journal of Biological Chemistry, 2007, vol. 282, No. 18, pp. 13552-13560.

Koziczak-Holbro, Magdalena, et al., "The Critical Role of Kinase Activity of Interleukin-1 Receptor-Associated Kinase 4 in Animal Models of Joint Inflammation", Arthritis & Rheumatism, 2009, vol. 60, No. 6, pp. 1661-1671.

Ku, Cheng-Lung, et al., "Selective predisposition to bacterial infections in IRAK-4-defi cient children: IRAK-4-dependent TLRs are otherwise redundant in protective immunity", The Journal of Experimental Medicine, 2007, vol. 204, No. 10, pp. 2407-2422.

Lin, Su-Chang, et al., "Helical assembly in the MyD88-IRAK4-IRAK2 complex in TLR/IL-1R signalling", Nature, 2010, vol. 465, pp. 885-890.

Maekawa, Yuchiro, et al., "Survival and Cardiac Remodeling After Myocardial Infarction Are Critically Dependent on the Host Innate Immune Interleukin-1 Receptor-Associated Kinase-4 Signaling A Regulator of Bone Marrow-Derived Dendritic Cells", Circulation, 2009, vol. 120, pp. 1401-1414.

Mann, Douglas L., "The Emerging Role of Innate Immunity in the Heart and Vascular System For Whom the Cell Tolls", Circ Res., 2011, vol. 108, pp. 1133-1145.

Ngo, Vu N., et al., "LETTER Oncogenically active MYD88 mutations in human lymphoma", Nature, 2011, vol. 470, pp. 115-122.

Picard, Capucine, et al., "Pyogenic Bacterial Infections in Humans with IRAK-4 Deficiency", Science, 2003, vol. 299, pp. 2076-2280.

Puente, Xose S., et al., "LETTER Whole-genome sequencing identifies recurrent mutations in chronic lymphocytic leukaemia", Nature, 2011, vol. 475, pp. 101-106.

Rekhter Mark, et al., "Genetic ablation of IRAK4 kinase activity inhibits vascular lesion formation", Biochemical and Biophysical Research Communications, 2008, vol. 367, pp. 642-648.

Seganish, W. Michael, "Inhibitors of interleukin-1 receptor-associated kinase 4 (IRAK4): a patent review (2012-2015)", Expert Opinion on Therapeutic Patents, 2016, vol. 26, No. 8, pp. 917-932.

Sims, et al., "The IL-1 Family: Regulators of Immunity", Nature Rev. Immunol., 2010, 10, 89-102.

Staschke, Kirk A., et al., "IRAK4 Kinase Activity Is Required for Th17 Differentiation and Th17-Mediated Disease1", The Journal of Immunology, 2009, vol. 183, pp. 568-577.

Suzuki, Nobutaka, et al., "Severe impairment of interleukin-1 and Toll-like receptor signalling in mice lacking IRAK-4", Letters to Nature, 2002, vol. 416, pp. 750-754.

Swantek, Jennifer L., "IL-1 Receptor-Associated Kinase Modulates Host Responsiveness to Endotoxin1", The Journal of Immunology, 2000, vol. 164, pp. 4301-4306.

Thomas, James A., et al., "Impaired Cytokine Signaling in Mice Lacking the IL-1 Receptor-Associated Kinase1", The Journal of Immunology, 1999, vol. 163, pp. 978-984.

Wan, Youzhong, et al., "Interleukin-1 Receptor-associated Kinase 2 Is Critical for Lipopolysaccharide-mediated Post-transcriptional Control", The Journal of Biological Chemistry, 2009, vol. 284, No. 16, pp. 10367-10375.

Wilke, Cailin Moira, et al., "Deciphering the role of Th17 cells in human disease", Trends in Immunology, 2011, vol. 32, No. 12, pp. 603-611.

* cited by examiner

THIENOPYRIDINES AND BENZOTHIOPHENES USEFUL AS IRAK4 INHIBITORS

CROSS REFERENCE TO RELATED APPLICATIONS

This application is a 371 application of International Application No. PCT/US2018/031945, filed May 10, 2018, which claims the benefit of U.S. Provisional Patent Application Ser. No. 62/504,956, filed May 11, 2017, the content of each is hereby fully incorporated herein in its entirety.

The present invention generally relates to thienopyridine and benzothiophene compounds useful as kinase inhibitors, including the modulation of IRAK-4. Provided herein are thienopyridine and benzothiophene compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including IRAK-4 in a mammal.

Toll/IL-1 receptor family members are important regulators of inflammation and host resistance. The Toll like receptor (TLR) family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Members of the IRAK family of serine/threonine kinases are recruited to the receptor via interactions with MyD88. The family consists of four members. Several lines of evidence indicate that IRAK4 plays a critical and non-redundant role in initiating signaling via MyD88 dependent TLRs and IL-1R family members. Structural data confirms that IRAK4 directly interacts with MyD88 and subsequently recruits either IRAK1 or IRAK2 to the receptor complex to facilitate downstream signaling (Lin, S. et al., *Nature*, 465: 885-890 (2010)). IRAK4 directly phosphorylates IRAK1 to facilitate downstream signaling to the E3 ubiquitin ligase TRAF6, resulting in activation of the serine/threonine kinase TAK1 with subsequent activation of the NFκB pathway and MAPK cascade (Flannery, S. et al., *Biochem. Pharmacol.*, 80:1981-1991 (2010)). A subset of human patients was identified who lack IRAK4 expression (Picard, C. et al., *Science*, 299:2076-2079 (2003)). Cells from these patients fail to respond to all TLR agonists with the exception of TLR3 as well as to members of the IL-1 family including IL-1β and IL-18 (Ku, C. et al., *J. Exp. Med.*, 204:2407-2422 (2007)). Deletion of IRAK4 in mice results in a severe block in IL-1, IL-18 and all TLR dependent responses with the exception of TLR3 (Suzuki, N. et al., *Nature*, 416:750-754 (2002)). In contrast, deletion of either IRAK1 (Thomas, J. A. et al., *J. Immunol.*, 163:978-984 (1999); Swantek, J. L. et al., *J. Immunol.*, 164:4301-4306 (2000) or IRAK2 (Wan, Y. et al., *J. Biol. Chem.*, 284:10367-10375 (2009)) results in partial loss of signaling. Furthermore, IRAK4 is the only member of the IRAK family whose kinase activity has been shown to be required for initiation of signaling. Replacement of wild type IRAK4 in the mouse genome with a kinase inactive mutant (KDKI) impairs signaling via all MyD88 dependent receptors including IL-1, IL-18 and all TLRs with the exception of TLR3 (Koziczak-Holbro, M. et al., *J. Biol. Chem.*, 282:13552-13560 (2007); Kawagoe, T. et al., *J. Exp. Med.*, 204:1013-1024 (2007); and Fraczek, J. et al., *J. Biol. Chem.*, 283:31697-31705 (2008)).

As compared to wild type animals, IRAK4 KDKI mice show greatly reduced disease severity in mouse models of multiple sclerosis (Staschke, K. A. et al., *J. Immunol.*, 183:568-577 (2009)), rheumatoid arthritis (Koziczak-Holbro, M. et al., *Arthritis Rheum.*, 60:1661-1671 (2009)), atherosclerosis (Kim, T. W. et al., *J. Immunol.*, 186:2871-2880 (2011) and Rekhter, M. et al., *Biochem. Biophys. Res. Comm.*, 367:642-648 (2008)), and myocardial infarction (Maekawa, Y. et al., *Circulation*, 120:1401-1414 (2009)). As described, IRAK4 inhibitors will block all MyD88 dependent signaling. MyD88 dependent TLRs have been shown to contribute to the pathogenesis of multiple sclerosis, rheumatoid arthritis, cardiovascular disease, metabolic syndrome, sepsis, systemic lupus erythematosus, inflammatory bowel diseases including Crohn's disease and ulcerative colitis, autoimmune uveitis, asthma, allergy, type I diabetes, and allograft rejection (Keogh, B. et al., *Trends Pharmacol. Sci.*, 32:435-442 (2011); Mann, D. L., *Circ. Res.*, 108:1133-1145 (2011); Horton, C. G. et al., *Mediators Inflamm.*, Article ID 498980 (2010), doi:10.1155/2010/498980; Goldstein, D. R. et al., *J. Heart Lung Transplant.*, 24:1721-1729 (2005); and Cario, E., *Inflamm. Bowel Dis.*, 16:1583-1597 (2010)). Oncogenically active MyD88 mutations in diffuse large B cell lymphomas have been identified that are sensitive to IRAK4 inhibition (Ngo, V. N. et al., *Nature*, 470:115-121 (2011)). Whole genome sequencing also identified mutations in MyD88 associated with chronic lymphatic leukemia suggesting that IRAK4 inhibitors may also have utility in treating leukemia (Puente, X. S. et al., *Nature*, 475:101-105 (2011)).

In addition to blocking TLR signaling, IRAK4 inhibitors will also block signaling by members of the IL-1 family. Neutralization of IL-1 has been shown to be efficacious in multiple diseases including gout; gouty arthritis; type 2 diabetes; auto-inflammatory diseases including Cryopyrin-Associated Periodic Syndromes (CAPS), TNF Receptor Associated Periodic Syndrome (TRAPS), Familial Mediterranean Fever (FMF), adult onset stills; systemic onset juvenile idiopathic arthritis; stroke; Graft-versus-Host Disease (GVHD); smoldering multiple myeloma; recurrent pericarditis; osteoarthritis; emphysema (Dinarello, C. A., *Eur. J. Immunol.*, 41:1203-1217 (2011) and Couillin, I. et al., *J. Immunol.*, 183:8195-8202 (2009)). In a mouse model of Alzheimer's disease, blockade of IL-1 receptor improved cognitive defects, attenuated tau pathology and reduced oligomeric forms of amyloid-β (Kitazawa, M. et al., *J. Immunol.*, 187:6539-6549 (2011)). IL-1 has also been shown to be a critical link to adaptive immunity, driving differentiation of the TH17 effector T cell subset (Chung, Y. et al., *Immunity*, 30:576-587 (2009)). Therefore, IRAK4 inhibitors are predicted to have efficacy in TH17 associated diseases including multiple sclerosis, psoriasis, inflammatory bowel diseases, autoimmune uveitis, and rheumatoid arthritis (Wilke, C. M. et al., *Trends Immunol.*, 32:603-661 (2011)).

WO2013/106612, WO2013/106614, WO2013/106641, WO2014/074657, and WO2014/074675 disclose substituted pyridyl compounds useful as kinase inhibitors, including the modulation of IRAK4.

In view of the conditions that may benefit by treatment involving modulation of protein kinases, it is immediately apparent that new compounds capable of modulating protein kinases such as IRAK-4 and methods of using these compounds could provide substantial therapeutic benefits to a wide variety of patients.

The present invention relates to a new class of thienopyridines and benzothiophene substituted compounds found to be effective inhibitors of protein kinases including IRAK-4. These compounds are provided to be useful as pharmaceuticals with desirable stability, bioavailability, therapeutic index, and toxicity values that are important to their drugability.

SUMMARY OF THE INVENTION

The present invention provides to compounds of Formula (I) that are useful as inhibitors of IRAK-4, and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of IRAK-4 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

One embodiment provides a method for treating inflammatory and autoimmune diseases wherein the treatment of inflammatory diseases is even more preferred. Particular, inflammatory and autoimmune diseases include, but are not limited to, Crohn's disease, ulcerative colitis, asthma, graft versus host disease, allograft rejection, chronic obstructive pulmonary disease, Graves' disease, rheumatoid arthritis, systemic lupus erythematosus, lupus nephritis, cutaneous lupus, psoriasis, cryopyrin-associated periodic syndromes (CAPS), TNF receptor associated periodic syndrome (TRAPS), familial Mediterranean fever (FMF), adult onset stills, systemic onset juvenile idiopathic arthritis, multiple sclerosis, neuropathic pain, gout, and gouty arthritis.

One embodiment provides a method for treating gout and gouty arthritis.

An alternate preferred embodiment is a method for treating metabolic diseases, including type 2 diabetes and atherosclerosis.

One embodiment provides a method for treating cancer comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancer.

The present invention also provides a compound of Formula (I) or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

DETAILED DESCRIPTION

The first aspect of the present invention provides at least one compound of Formula (I):

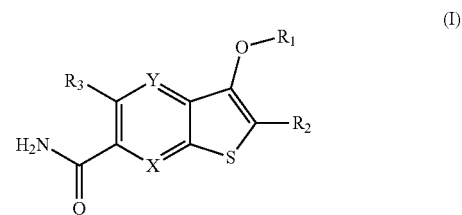

or a salt or prodrug thereof, wherein:
X is $CR_4$ or N;
Y is $CR_5$ or N; provided that only one of X and Y is N;
$R_1$ is:

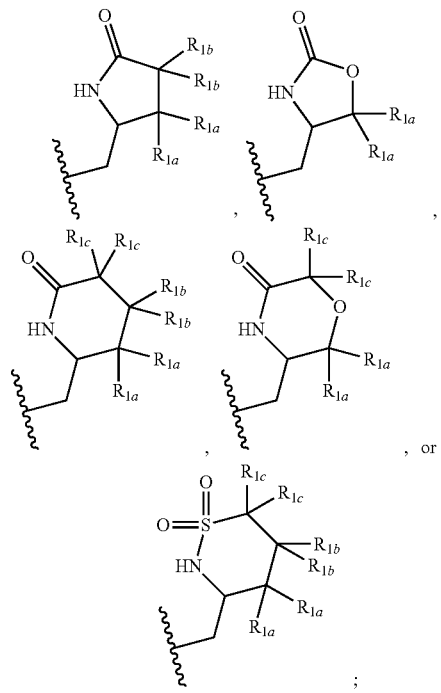

each $R_{1a}$ is independently H, —OH, F, $C_{1-3}$ alkyl, $C_{1-3}$ fluoroalkyl, $C_{1-3}$ alkoxy, $C_{1-3}$ fluoroalkoxy, or $C_{3-6}$ cycloalkyl; or two $R_{1a}$ along with the carbon atom to which they are attached, can form a 3- to 4-membered spirocycloalkyl ring;

each $R_{1b}$ is independently H, —OH, F, $C_{1-3}$ alkyl, $C_{1-3}$ fluoroalkyl, $C_{1-3}$ alkoxy, $C_{1-3}$ fluoroalkoxy, or $C_{3-6}$ cycloalkyl; or two $R_{1b}$ along with the carbon atom to which they are attached, can form a 3- to 4-membered spirocycloalkyl ring;

each $R_{1c}$ is independently H, —OH, F, $C_{1-3}$ alkyl, $C_{1-3}$ fluoroalkyl, $C_{1-3}$ alkoxy, $C_{1-3}$ fluoroalkoxy, or $C_{3-6}$ cycloalkyl; or two $R_{1c}$ along with the carbon atom to which they are attached, can form a 3- to 4-membered spirocycloalkyl ring;

$R_{1a}$ and $R_{1b}$ along with the carbon atoms to which they are attached, can form a 3- to 4-membered cycloalkyl ring;

$R_{1b}$ and $R_{1c}$ along with the carbon atoms to which they are attached, can form a 3- to 4-membered cycloalkyl ring;

$R_2$ is H, halo, $C_{1-3}$ alkyl, or $C_{3-6}$ cycloalkyl;

$R_3$ is $C_{1-4}$ alkoxy, $C_{1-4}$ fluoroalkoxy, or $C_{3-6}$ cycloalkoxy;

$R_4$ is H, halo, $C_{1-4}$ alkyl, $C_{1-4}$ fluoroalkyl, or $C_{3-6}$ cycloalkyl; and $R_5$ is H, halo, $C_{1-4}$ alkyl, $C_{1-4}$ fluoroalkyl, or $C_{3-6}$ cycloalkyl.

In one embodiment, a compound of Formula (I) or a salt or a prodrug thereof is provided wherein X is $CR_4$; Y is $CR_5$; and $R_1$, $R_2$, $R_3$, $R_4$, and $R_5$ are defined in the first aspect. Compounds of this embodiment have the structure of Formula (II):

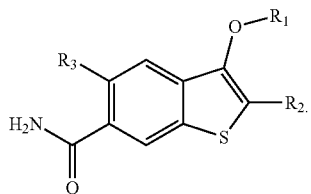

(II)

In one embodiment, a compound of Formula (I) or a salt or a prodrug thereof is provided wherein X is N; Y is $CR_5$; and $R_1$, $R_2$, $R_3$, and $R_5$ are defined in the first aspect.

Compounds of this embodiment have the structure of Formula (III):

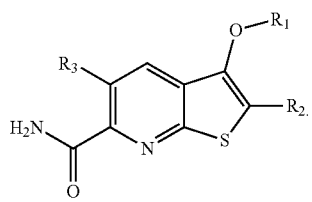

(III)

In one embodiment, a compound of Formula (I) or a salt or a prodrug thereof is provided wherein X is $CR_4$; Y is N; and $R_1$, $R_2$, $R_3$, and $R_4$ are defined in the first aspect. Compounds of this embodiment have the structure of Formula (IV):

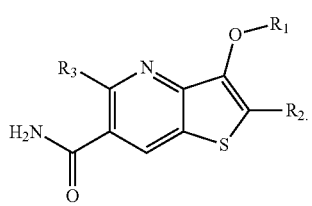

(IV)

In one embodiment, a compound of Formula (I) or a salt or a prodrug thereof is provided wherein $R_1$ is:

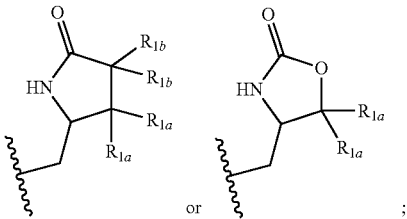

and X, Y, $R_2$, $R_3$, $R_{1a}$, and $R_{1b}$ are defined in the first aspect. Included in this embodiment are compounds in which $R_1$ is

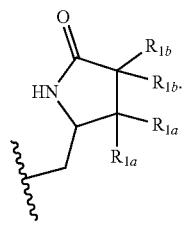

Also included in this embodiment are compounds in which $R_1$ is

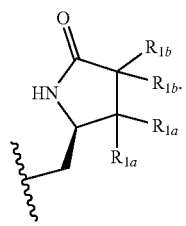

In one embodiment, a compound of Formula (I) or a salt or a prodrug thereof is provided wherein $R_1$ is:

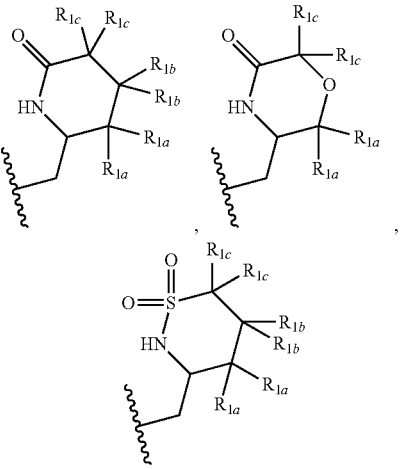

and X, Y, $R_2$, $R_3$, $R_{1a}$, $R_{1b}$, and $R_{1c}$ are defined in the first aspect. Included in this embodiment are compounds in which $R_1$ is

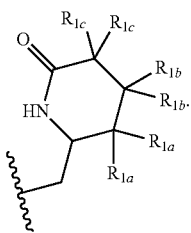

In one embodiment, a compound of Formula (I) or a salt or a prodrug thereof is provided wherein $R_1$ is:

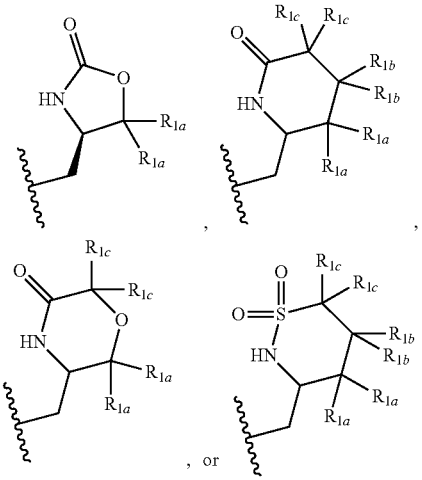

, or ;

and X, Y, $R_{1a}$, $R_{1b}$, $R_{1c}$, $R_2$, $R_3$, $R_4$, and $R_5$ are defined in the first aspect. Included in this embodiment are compounds in which each $R_{1a}$ is independently H or $C_{1-2}$ alkyl; each $R_{1b}$ is independently H, F, —$CH_3$, —$CHF_2$, or cyclopropyl; and each $R_{1c}$ is H.

In one embodiment, a compound of Formula (I) or a salt or a prodrug thereof is provided wherein each $R_{1a}$ is independently H, —OH, F, $C_{1-3}$ alkyl, $C_{1-3}$ fluoroalkyl, $C_{1-3}$ alkoxy, $C_{1-3}$ fluoroalkoxy, or $C_{3-6}$ cycloalkyl; and X, Y, $R_1$, $R_2$, and $R_3$ are defined in the first aspect. Included in this embodiment are compounds in which each $R_{1a}$ is independently H, —OH, F, $C_{1-3}$ alkyl, $C_{1-2}$ fluoroalkyl, $C_{1-2}$ alkoxy, $C_{1-2}$ fluoroalkoxy, or $C_{3-6}$ cycloalkyl. Also included in this embodiment are compounds in which each $R_{1a}$ is independently H or $C_{1-2}$ alkyl; and compounds in which one $R_{1a}$ is H, and the other $R_{1a}$ is —OH, F, $C_{1-3}$ alkyl, $C_{1-3}$ fluoroalkyl, $C_{1-3}$ alkoxy, $C_{1-3}$ fluoroalkoxy, or $C_{3-6}$ cycloalkyl.

In one embodiment, a compound of Formula (I) or a salt or a prodrug thereof is provided wherein two $R_{1a}$ along with the carbon atom to which they are attached, form a 3- to 4-membered spirocycloalkyl ring; and X, Y, $R_1$, $R_2$, and $R_3$ are defined in the first aspect. Included in this embodiment are compounds in which two $R_{1a}$ along with the carbon atom to which they are attached, form a 3-membered spirocycloalkyl ring. Also included in this embodiment are compounds in which two $R_{1a}$ along with the carbon atom to which they are attached, form a 4-membered spirocycloalkyl ring.

In one embodiment, a compound of Formula (I) or a salt or a prodrug thereof is provided wherein each $R_{1b}$ is independently H, —OH, F, $C_{1-3}$ alkyl, $C_{1-3}$ fluoroalkyl, $C_{1-3}$ alkoxy, $C_{1-3}$ fluoroalkoxy, or $C_{3-6}$ cycloalkyl; and X, Y, $R_1$, $R_2$, and $R_3$ are defined in the first aspect. Included in this embodiment are compounds in which each $R_{1b}$ is independently H, —OH, F, $C_{1-3}$ alkyl, $C_{1-2}$ fluoroalkyl, $C_{1-2}$ alkoxy, $C_{1-2}$ fluoroalkoxy, or $C_{3-6}$ cycloalkyl. Also included in this embodiment are compounds in which each $R_{1b}$ is independently H, F, —$CH_3$, —$CHF_2$, or cyclopropyl; and compounds in which one $R_{1b}$ is H, and the other $R_{1b}$ is F, —$CH_3$, —$CHF_2$, or cyclopropyl. Additionally, included in this embodiment are compounds in which each $R_{1b}$ is H; each $R_{1b}$ is F; and compounds in which each $R_{1b}$ is —$CH_3$.

In one embodiment, a compound of Formula (I) or a salt or a prodrug thereof is provided wherein two $R_{1b}$ along with the carbon atom to which they are attached, form a 3- to 4-membered spirocycloalkyl ring; and X, Y, $R_1$, $R_2$, and $R_3$ are defined in the first aspect. Included in this embodiment are compounds in which two $R_{1b}$ along with the carbon atom to which they are attached, form a 3-membered spirocycloalkyl ring. Also included in this embodiment are compounds in which two $R_{1b}$ along with the carbon atom to which they are attached, form a 4-membered spirocycloalkyl ring.

In one embodiment, a compound of Formula (I) or a salt or a prodrug thereof is provided wherein $R_1$ is:

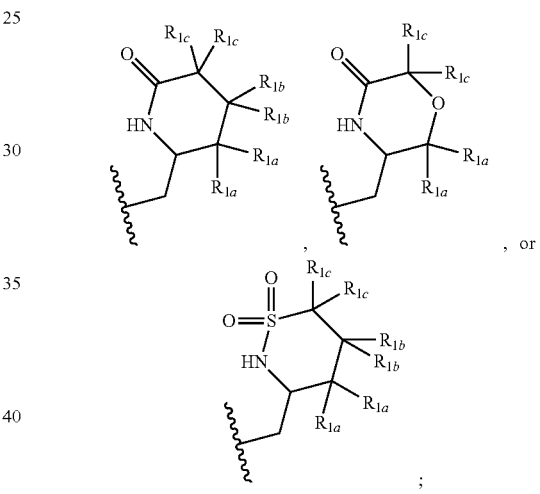

, or ;

each $R_{1c}$ is independently H, —OH, F, $C_{1-3}$ alkyl, $C_{1-3}$ fluoroalkyl, $C_{1-3}$ alkoxy, $C_{1-3}$ fluoroalkoxy, or $C_{3-6}$ cycloalkyl; and X, Y, $R_2$, and $R_3$ are defined in the first aspect. Included in this embodiment are compounds in which each $R_{1c}$ is independently H, —OH, F, $C_{1-3}$ alkyl, $C_{1-2}$ fluoroalkyl, $C_{1-2}$ alkoxy, $C_{1-2}$ fluoroalkoxy, or $C_{3-6}$ cycloalkyl. Also included in this embodiment are compounds in which each $R_{1c}$ is independently H or $C_{1-2}$ alkyl; and compounds in which each $R_{1c}$ is H.

In one embodiment, a compound of Formula (I) or a salt or a prodrug thereof is provided wherein $R_1$ is:

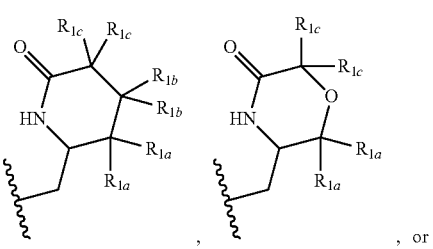

, or

-continued

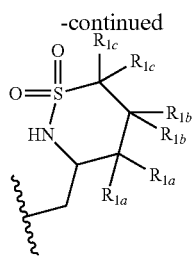

two $R_{1c}$ along with the carbon atom to which they are attached, form a 3- to 4-membered spirocycloalkyl ring; and X, Y, $R_{1a}$, $R_{1b}$, $R_2$, and $R_3$ are defined in the first aspect. Included in this embodiment are compounds in which two $R_{1c}$ along with the carbon atom to which they are attached, form a 3-membered spirocycloalkyl ring. Also included in this embodiment are compounds in which two $R_{1c}$ along with the carbon atom to which they are attached, form a 4-membered spirocycloalkyl ring.

In one embodiment, a compound of Formula (I) or a salt or a prodrug thereof is provided wherein $R_{1a}$ and $R_{1b}$ along with the carbon atoms to which they are attached, form a 3- to 4-membered cycloalkyl ring; each $R_{1b}$ is independently H, OH, F, $C_{1-3}$ alkyl, $C_{1-3}$ fluoroalkyl, $C_{1-3}$ alkoxy, $C_{1-3}$ fluoroalkoxy, or $C_{3-6}$ cycloalkyl; and X, Y, $R_1$, $R_2$, and $R_3$ are defined in the first aspect. Included in this embodiment are compounds in which $R_{1a}$ and $R_{1b}$ along with the carbon atoms to which they are attached, form a 3-membered cycloalkyl ring. Also, included in this embodiment are compounds in which $R_{1a}$ and $R_{1b}$ along with the carbon atoms to which they are attached, form a 4-membered cycloalkyl ring.

In one embodiment, a compound of Formula (I) or a salt or a prodrug thereof is provided wherein $R_1$ is:

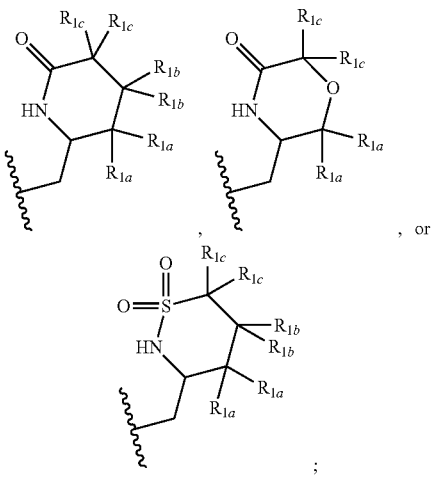

each $R_{1a}$ is independently H, OH, F, $C_{1-3}$ alkyl, $C_{1-3}$ fluoroalkyl, $C_{1-3}$ alkoxy, $C_{1-3}$ fluoroalkoxy, or $C_{3-6}$ cycloalkyl; $R_{1c}$ and $R_{1c}$ along with the carbon atoms to which they are attached, form a 3- to 4-membered cycloalkyl ring; and X, Y, $R_2$, and $R_3$ are defined in the first aspect. Included in this embodiment are compounds in which $R_{1b}$ and $R_{1c}$ along with the carbon atoms to which they are attached, form a 3-membered cycloalkyl ring. Also, included in this embodiment are compounds in which $R_{1b}$ and $R_{1c}$ along with the carbon atoms to which they are attached, form a 4-membered cycloalkyl ring.

In one embodiment, a compound of Formula (I) or a salt or a prodrug thereof is provided wherein $R_3$ is $C_{1-3}$ alkoxy, $C_{1-2}$ fluoroalkoxy, or $C_{3-6}$ cycloalkoxy; and X, Y, $R_1$, $R_2$, $R_4$, and $R_5$ are defined in the first aspect. Included in this embodiment are compounds in which $R_3$ is $C_{1-3}$ alkoxy and $C_{3-6}$ cycloalkoxy. Also included in this embodiment are compounds in which $R_3$ is —$OCH_3$, —$OCH(CH_3)_2$, or —$O(cyclopropyl)$.

In one embodiment, a compound of Formula (I) or a salt or a prodrug thereof is provided wherein X is $CR_4$; $R_4$ is H, halo, $C_{1-4}$ alkyl, $C_{1-4}$ fluoroalkyl, or $C_{3-6}$ cycloalkyl; and Y, $R_1$, $R_2$, $R_3$, and $R_5$ are defined in the first aspect. Included in this embodiment are compounds in which $R_4$ is H, F, $C_{1-2}$ alkyl, $C_{1-2}$ fluoroalkyl, or $C_{3-6}$ cycloalkyl. Also included in this embodiment are compounds in which $R_4$ is H, F, —$CH_3$, or —$CF_3$; and compounds in which $R_4$ is H.

In one embodiment, a compound of Formula (I) or a salt or a prodrug thereof is provided wherein Y is $CR_5$; $R_5$ is H, halo, $C_{1-4}$ alkyl, $C_{1-4}$ fluoroalkyl, or $C_{3-6}$ cycloalkyl; and Y, $R_1$, $R_2$, $R_3$, and $R_4$ are defined in the first aspect. Included in this embodiment are compounds in which $R_5$ is H, F, $C_{1-2}$ alkyl, $C_{1-2}$ fluoroalkyl, or $C_{3-6}$ cycloalkyl. Also included in this embodiment are compounds in which $R_5$ is H, F, —$CH_3$, or —$CF_3$; and compounds in which $R_5$ is H.

In one embodiment, a compound of Formula (I) or a salt or a prodrug thereof is provided wherein each $R_{1a}$ is independently H, —OH, F, $C_{1-3}$ alkyl, $C_{1-2}$ fluoroalkyl, $C_{1-2}$ alkoxy, $C_{1-2}$ fluoroalkoxy, or $C_{3-6}$ cycloalkyl; or two $R_{1a}$ along with the carbon atom to which they are attached, can form a 3- to 4-membered spirocycloalkyl ring; each $R_{1b}$ is independently H, —OH, F, $C_{1-2}$ alkyl, $C_{1-2}$ fluoroalkyl, $C_{1-2}$ alkoxy, $C_{1-2}$ fluoroalkoxy, or $C_{3-6}$ cycloalkyl; or two $R_{1b}$ along with the carbon atom to which they are attached, can form a 3- to 4-membered spirocycloalkyl ring; each $R_{1c}$ is independently H, F, $C_{1-2}$ alkyl, $C_{1-2}$ fluoroalkyl, or $C_{3-6}$ cycloalkyl; or two $R_{1c}$ along with the carbon atom to which they are attached, can form a 3- to 4-membered spirocycloalkyl ring; $R_2$ is H, F, Cl, $C_{1-2}$ alkyl, or $C_{3-6}$ cycloalkyl; $R_3$ is $C_{1-3}$ alkoxy, $C_{1-2}$ fluoroalkoxy, or $C_{3-6}$ cycloalkoxy; $R_4$ is H, halo, $C_{1-4}$ alkyl, $C_{1-4}$ fluoroalkyl, or $C_{3-6}$ cycloalkyl; $R_5$ is H, halo, $C_{1-4}$ alkyl, $C_{1-4}$ fluoroalkyl, or $C_{3-6}$ cycloalkyl; and X, Y, and $R_1$ are defined in the first aspect. Included in this embodiment are compounds in which X is CH. Also included in this embodiment are compounds in which X is CH; and Y is N.

In one embodiment, a compound of Formula (I) or a salt or a prodrug thereof is provided wherein each $R_{1a}$ is independently H or $C_{1-2}$ alkyl; each $R_{1b}$ is independently H, F, —$CH_3$, —$CHF_2$, or cyclopropyl; or two $R_{1b}$ along with the carbon atom to which they are attached, can form a 3-membered spirocycloalkyl ring; each $R_{1c}$ is H; $R_2$ is H or —$CH_3$; $R_3$ is —$OCH_3$, —$OCH(CH_3)_2$, or —$O(cyclopropyl)$; $R_4$ is H; $R_5$ is H; and X, Y, and $R_1$ are defined in the first aspect. Included in this embodiment are compounds in which X is CH. Also included in this embodiment are compounds in which X is CH; and Y is N.

In one embodiment, a compound of Formula (I) or a salt or a prodrug thereof is provided wherein each $R_{1a}$ is independently H or $C_{1-2}$ alkyl; each $R_{1b}$ is independently H, F, —$CH_3$, —$CHF_2$, or cyclopropyl; or two $R_{1b}$ along with the carbon atom to which they are attached form a 3-membered spirocycloalkyl ring; and X, Y, $R_1$, $R_2$, $R_3$, $R_4$, and $R_5$ are defined in the first aspect. Included in this embodiment are compounds in which X is CH. Also included in this embodiment are compounds in which X is CH; and Y is N.

In one embodiment, a compound of Formula (I) or a salt or a prodrug thereof is provided wherein X is CH; Y is N; $R_1$ is:

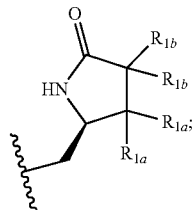

and $R_{1a}$, $R_{1b}$, $R_2$, $R_3$, $R_4$, $R_5$ are defined in the first aspect. Included in this embodiment are compounds in which $R_4$ is H; and $R_5$ is H. Also included are compounds in which one $R_{1a}$ is H and the other $R_{1a}$ is H or $C_{1-2}$ alkyl.

One embodiment provides a compound of Formula (I) or a salt thereof, wherein said compound is selected from: 3-(((2S,3S)-3-ethyl-4,4-difluoro-5-oxopyrrolidin-2-yl)methoxy)-5-methoxythieno[3,2-b]pyridine-6-carboxamide (1); 3-(((2S,3S,4S)-3-ethyl-4-fluoro-5-oxopyrrolidin-2-yl)methoxy)-5-methoxythieno[3,2-b]pyridine-6-carboxamide (2); (S)-5-methoxy-3-((5-oxopyrrolidin-2-yl)methoxy)thieno[2,3-b]pyridine-6-carboxamide (3); 3-(((2S,3S,4S)-3-ethyl-4-fluoro-5-oxopyrrolidin-2-yl)methoxy)-5-methoxybenzo[b]thiophene-6-carboxamide (4); (S)-5-methoxy-3-((5-oxopyrrolidin-2-yl) methoxy)thieno[3,2-b]pyridine-6-carboxamide (5); 3-(((2S,3R)-3-ethyl-5-oxopyrrolidin-2-yl)methoxy)-5-methoxythieno[3,2-b]pyridine-6-carboxamide (6); 5-methoxy-3-((5-oxomorpholin-3-yl)methoxy)thieno[3,2-b]pyridine-6-carboxamide (7); 3-(((2S,3S,4R)-3-ethyl-4-fluoro-5-oxopyrrolidin-2-yl)methoxy)-5-methoxythieno[3,2-b]pyridine-6-carboxamide (8); 3-(46S,7R)-7-ethyl-4-oxo-5-azaspiro[2.4]heptan-6-yl)methoxy)-5-methoxythieno[3,2-b]pyridine-6-carboxamide (9); 3-(((2S,3R)-3-ethyl-4,4-dimethyl-5-oxopyrrolidin-2-yl)methoxy)-5-methoxythieno[3,2-b]pyridine-6-carboxamide (10); 3-(((2S,4R)-4-fluoro-5-oxopyrrolidin-2-yl)methoxy)-5-methoxythieno[3,2-b]pyridine-6-carboxamide (11); 3-((2S,3R)-3-(difluoromethyl)-5-oxopyrrolidin-2-yl)methoxy)-5-methoxythieno[3,2-b]pyridine-6-carboxamide (12); 5-methoxy-3-(((2S)-4-methyl-5-oxopyrrolidin-2-yl)methoxy)thieno[3,2-b]pyridine-6-carboxamide (13-14); 3-(((2S)-4-ethyl-5-oxopyrrolidin-2-yl)methoxy)-5-methoxythieno[3,2-b]pyridine-6-carboxamide (15-16); 5-methoxy-3-(((2S,3R)-3-methyl-5-oxopyrrolidin-2-yl)methoxy)thieno[3,2-b]pyridine-6-carboxamide (17); 3-(((2S,3S,4R)-3-cyclopropyl-4-fluoro-5-oxopyrrolidin-2-yl)methoxy)-5-methoxythieno[3,2-b]pyridine-6-carboxamide (18); 3-(((2S,3R)-3-ethyl-5-oxopyrrolidin-2-yl)methoxy)-5-methoxy-2-methylthieno[3,2-b]pyridine-6-carboxamide (19); 5-cyclopropoxy-3-(((2S,3R)-3-ethyl-5-oxopyrrolidin-2-yl)methoxy)thieno[3,2-b]pyridine-6-carboxamide (20); 3-(((2S,3S)-4,4-difluoro-3-methyl-5-oxopyrrolidin-2-yl) methoxy)-5-methoxythieno[3,2-b]pyridine-6-carboxamide (21); 3-(((2S,3S,4S)-3-ethyl-4-fluoro-5-oxopyrrolidin-2-yl)methoxy)-5-methoxy-2-methylthieno[3,2-b]pyridine-6-carboxamide (22); 3-(((2S,3S,4S)-3-ethyl-4-fluoro-5-oxopyrrolidin-2-yl)methoxy)-5-isopropoxythieno[3,2-b]pyridine-6-carboxamide (23); 5-cyclopropoxy-3-(((2S,3S,4S)-3-ethyl-4-fluoro-5-oxopyrrolidin-2-yl)methoxy)thieno[3,2-b]pyridine-6-carboxamide (24); (S)-5-methoxy-2-methyl-3-((5-oxopyrrolidin-2-yl)methoxy)thieno[3,2-b]pyridine-6-carboxamide (25); 3-(((4R,5S)-5-ethyl-2-oxooxazolidin-4-yl)methoxy)-5-methoxythieno[3,2-b]pyridine-6-carboxamide (26); 3-(((2S,3S,4R)-4-fluoro-3-methyl-5-oxopyrrolidin-2-yl)methoxy)-5-methoxythieno[3,2-b]pyridine-6-carboxamide (27); 3-(((2S,3S,4S)-4-fluoro-3-methyl-5-oxopyrrolidin-2-yl) methoxy)-5-methoxythieno[3,2-b]pyridine-6-carboxamide (28); and 3-(42S,3R)-3-ethyl-5-oxopyrrolidin-2-yl)methoxy)-5-methoxybenzo[b]thiophene-6-carboxamide (29).

One embodiment provides compounds of the Formula (I) having IRAK4 $IC_{50}$ values of ≤0.6 μM.

One embodiment provides compounds of the Formula (I) having IRAK4 $IC_{50}$ values of ≤0.1 μM.

One embodiment provides compounds of the Formula (I) having IRAK4 $IC_{50}$ values of ≤0.05 μM.

One embodiment provides compounds of the Formula (I) having IRAK4 $IC_{50}$ values of ≤0.025 μM.

One embodiment provides compounds of the Formula (I) having IRAK4 $IC_{50}$ values of ≤0.015 μM.

One embodiment provides compounds of the Formula (I) having IRAK4 $IC_{50}$ values of ≤0.01 μM.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms. The term "alkoxy," as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "spirocycloalkyl" refers to a carbocyclyl ring attached to the molecular moiety by a carbon atom in the cycloalkyl ring that is shared with the molecular moiety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to IRAK4; or effective to treat or prevent autoimmune and/or inflammatory disease states, such as multiple sclerosis and rheumatoid arthritis; or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

UTILITY

The compounds of the invention modulate kinase activity, including the modulation of IRAK-4. Other types of kinase activity that may be modulated by the compounds of the instant invention include, but are not limited to, the Pelle/IRAK family and mutants thereof.

Accordingly, compounds of Formula (I) have utility in treating conditions associated with the modulation of kinase activity, and particularly the selective inhibition of IRAK-4 activity or the inhibition of IRAK and other Pelle family kinases. Such conditions include TLR/IL-1 family receptor associated diseases in which cytokine levels are modulated as a consequence of intracellular signaling. Moreover, the compounds of Formula (I) have advantageous selectivity for IRAK-4 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors IRAK-4, compounds of Formula (I) are useful in treating TLR/IL-1 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional IRAK-4-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

When the terms "IRAK-4-associated condition" or "IRAK-4-associated disease or disorder" are used herein, each is intended to encompass all of the conditions identified above as if repeated at length, as well as any other condition that is affected by IRAK-4 kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit IRAK-4 and/or treat diseases.

The methods of treating IRAK-4 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit IRAK-4 and/or treat diseases associated with IRAK-4.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IRAK-4 kinase-associated conditions, including TLR and IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, diuresis, and/or natriuresis. In another embodiment, the package insert states that the pharmaceutical composition can be used in combination (as defined previously) with a second therapeutic agent to treat cardiovascular disorder, diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

METHODS OF PREPARATION

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of the Formula (I) can be prepared according to the methods outlined in the following schemes. In Scheme 1, the thienopyridine intermediate 1.2 can be prepared from oxime 1.1 as described in US2010/298334. Treatment of intermediate 1.2 with various alkoxides such as sodium methoxide in solvents such as methanol can afford the corresponding alkoxy intermediates 1.3 (R3=OCH$_3$, for example). Introduction of a halo group such as a bromo at the 3-position of 1.3 affords 1.4 which can accomplished by treatment with N-bromosuccinimide in solvents such as DMF. The bromo group of 1.4 can be replaced with a hydroxyl group via direct treatment of 1.4 with water in the presence of Rock Phos PD G3 and cesium carbonate in solvents such as dioxane affording 1.5. Alternatively, 1.5 can be prepared in 2 steps from 1.4 via the corresponding boronic acid 1.6. Treatment of 1.4 with bis-pinacolatodiboron in the presence of PdCl$_2$(dppf)-CH$_2$Cl$_2$ adduct and potassium acetate in solvents such as dioxane affords 1.6 which can be converted to 1.5 via treatment with hydrogen peroxide in the presence of a base such as sodium or potassium carbonate in solvents such as THF and water.

Coupling of the hydroxy compound 1.5 with intermediates encompassing R groups of the compounds of Formula I can be carried out by nucleophilic displacement reactions at RX, where X is tosylate, mesylate or a halide such as chloride or bromide. Alternatively, 1.5 can be coupled directly with alcohols ROH via the Mitsunobu reaction affording 1.7. Treatment of 1.7 with potassium carbonate and hydrogen peroxide in solvents such as DMSO affords compound of Formula I.

SCHEME 1

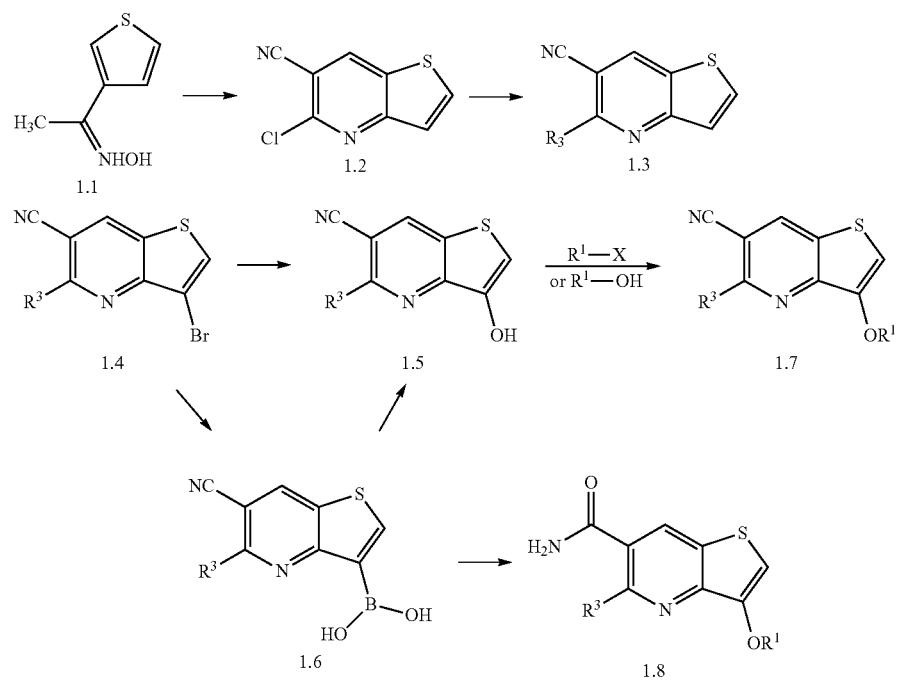

Certain compounds of Formula I can be prepared as outlined in Scheme 2. Displacement of the chloro group at the 2 position of compound 2.1 with an ester of mercaptoacetic acid in the presence of a base such as LiHMDS in solvents such as THF affords intermediate 2.2. Conversion of 2.2 to 2.3 can be accomplished by treatment with a base such as DBU in toluene. Hydrolysis of the nitrile 2.3 to afford the primary amide 2.4 can be accomplished with by treatment with an acid such as concentrated sulfuric acid. Compound 2.4 can be converted to 2.5 by treatment with potassium t-butoxide in DMSO at about 80° C. Coupling of 2.5 with $R^1OH$ or $R^1X$ as described for Scheme 1 can provide compounds of the formula 2.6. Compound 2.6 can be converted to 2.7 by nucleophilic displacement of the chloro group to afford compounds of the general Formula I.

SCHEME 2

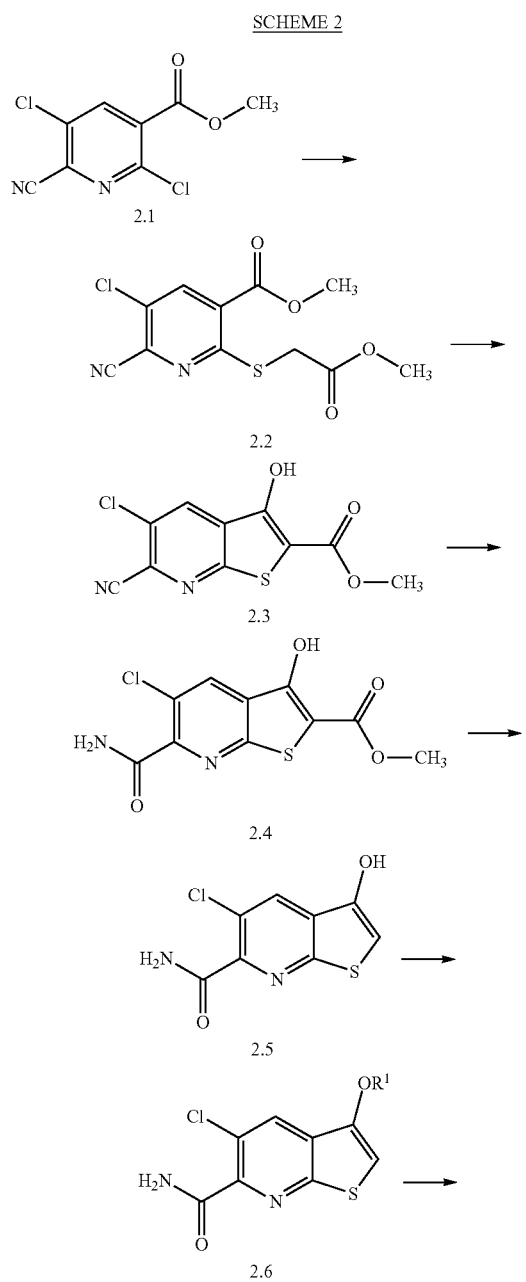

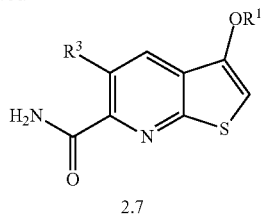

2.7

Certain compounds of Formula I can be prepared as outlined in Scheme 3. Alkylation of the thiol 3.1 with bromoacetaldehyde diethyl acetal in the presence of a base such as potassium carbonate in solvents such as DMF affords 3.2 which can converted to the benzothiophene 3.3 via heating in solvents such as chlorobenzene in the presence of polyphosphoric acid. The reaction may generate a mixture of 3.3 and the corresponding regioisomeric product. Conversion of the bromo group of 3.3 to cyano to generate 3.4 can be accomplished by treatment with zinc cyanide in the presence of palladium tetrakis in solvents such as DMF. The nitrile 3.4 can be converted to the corresponding compounds of Formula I via the sequence described for Scheme I.

SCHEME 3

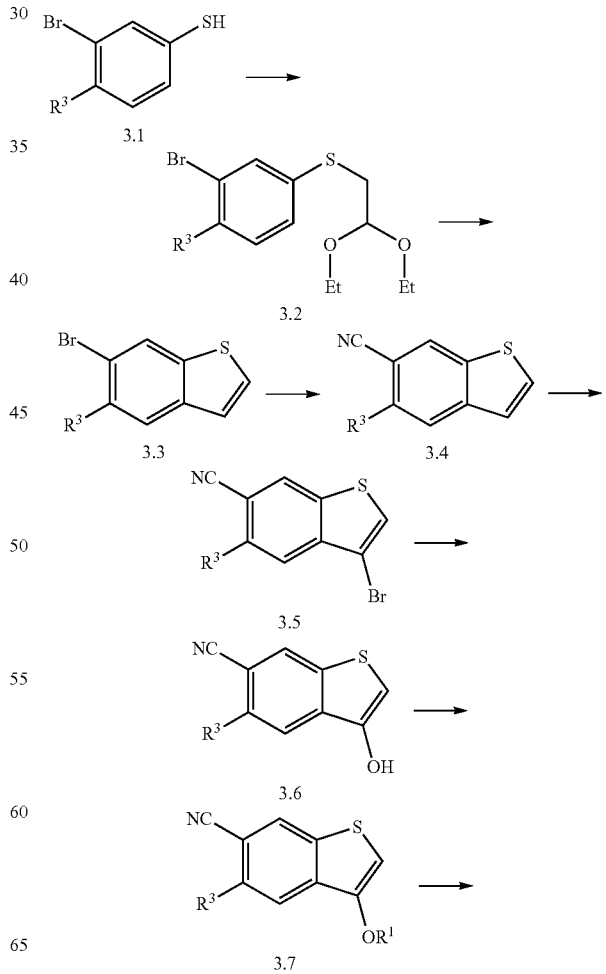

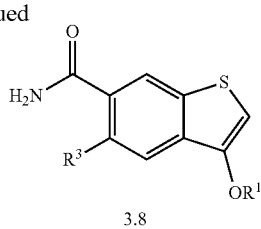

3.8

EXAMPLES

Compounds of the current invention and intermediates used in the preparation of compounds of the current invention can be prepared using procedures shown in the following examples and related procedures. The methods and conditions used in these examples, and the actual compounds prepared in these examples, are not meant to be limiting, but are meant to demonstrate how the compounds of the current invention can be prepared. Starting materials and reagents used in these examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters Sunfire $C_{18}$, Waters Xbridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

ABBREVIATIONS aq. aqueous
brine saturated aqueous sodium chloride
DBU 1,8-diazabicyclo[5.4.0]undec-7-ene
DCM dichloromethane
DMF N,N-dimethylformamide
DMSO dimethyl sulfoxide
DPPF 1,1'-bis(diphenylphosphino)ferrocene
Et ethyl
EtOAc ethyl acetate
EtOH ethanol
g gram(s)
h hour(s)
HPLC High Performance Liquid Chromatography
LC/MS Liquid Chromatography-Mass Spectroscopy
LiHMDS lithium bis(trimethylsilyl)amide
MeCN acetonitrile
MeOH methanol
NBS N-bromosuccinimide
$PdCl_2(dppf)-CH_2Cl_2$ [1,1'-bis(diphenylphosphino)ferrocene]dichloropalladium(II) complex with dichloromethane
PPA polyphosphoric acid
TEA triethylamine
TFA trifluoroacetic acid
THF tetrahydrofuran
HPLC and LC/MS Methods:
Method A: Waters Acquity UPLC BEH C18 column (2.1×50 mm), 5:95 MeCN-water each with 10 mM ammonium acetate to 95:5 MeCN-water each with 10 mM ammonium acetate gradient at 0.8 mL/min over 1 minute, then a 0.5 min hold, 50° C. column temperature.
Method B: Waters Acquity UPLC BEH C18 column (2.1×50 mm), 2:98:0.1 MeCN-water-TFA to 98:2:0.1 MeCN-water-TFA gradient at 0.8 mL/min over 1 minute, then a 0.5 min hold, 50° C. column temperature.
Method C: Waters Acquity UPLC BEH C18 column (2.1×50 mm), 5:95:0.1 MeCN-water-TFA to 95:5:0.1 MeCN-water-TFA gradient at 1 mL/min over 3 minute, then a 0.75 min hold, 50° C. column temperature.

Example 1

3-(((2S,3S)-3-Ethyl-4,4-difluoro-5-oxopyrrolidin-2-yl)methoxy)-5-methoxythieno[3,2-b]pyridine-6-carboxamide

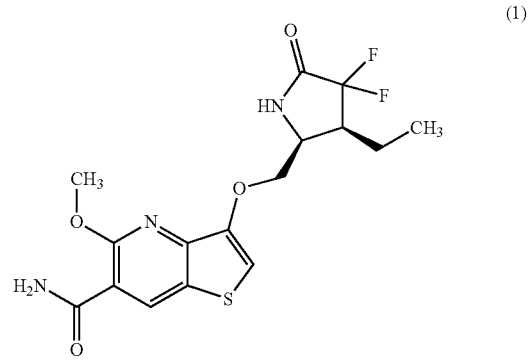 [SMILES: CC[C@H]1[C@@H](COc2csc3cc(C(N)=O)c(OC)nc23)NC(=O)C1(F)F]

Intermediate 1A: 5-Chlorothieno[3,2-b]pyridine-6-carbonitrile

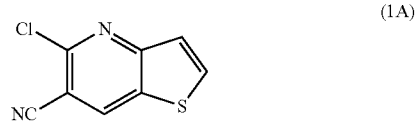 [SMILES: N#Cc1cc2sccc2nc1Cl]

To a solution of 1-(thiophen-3-yl)ethanone (25 g, 198 mmol) in ethanol (450 mL) and water (150 mL) was added hydroxylamine hydrochloride (27.5 g, 396 mmol) followed by the addition of sodium acetate (32.5 g, 396 mmol). The mixture was gently refluxed for 4 h and allowed to come to room temperature. Ice-cold water (200 mL) was then added and the mixture was stored at 4° C. overnight. The precipitate was collected by filtration to afford (Z)-1-(thiophen-3-yl)ethanone oxime (26.5 g, 95% yield) as a white solid.

POCl$_3$ (46.5 mL, 0.499 mol) was added dropwise to a stirred solution of (Z)-1-(thiophen-3-yl)ethanone oxime (7.06 g, 0.05 mol) in ether (0.3 L) at 7-10° C. (PCT Int. Appl. 2010 13565). The mixture was stirred at 7-10° C. for 2 h followed by dropwise addition of DMF (12 mL, 0.155 mol). The reaction mixture was heated to distill off most of the ether, until the internal temperature gradually reached 110° C. The mixture was heated at 110° C. for an additional 1 h. Hydroxylamine hydrochloride (6.95 g, 0.100 mol) was then carefully added in small portions at ca. 110° C. and the mixture was stirred for an additional 20 min period at 110° C. The mixture was allowed to cool to room temperature.

The mixture was poured slowly into a stirred mixture of ice and water. The precipitated brown solid was isolated by filtration. The reaction was repeated so that a total of 27 g of (Z)-1-(thiophen-3-yl)ethanone oxime was consumed affording 5-chlorothieno[3,2-b]pyridine-6-carbonitrile (13.5 g).

Intermediate 1B: 5-Methoxythieno[3,2-b]pyridine-6-carbonitrile

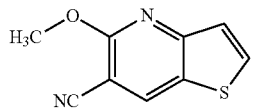

(1B)

A suspension of 5-chlorothieno[3,2-b]pyridine-6-carbonitrile (1.71 g, 8.79 mmol) and sodium methoxide (25% in MeOH) (2.130 mL, 9.31 mmol) in MeOH (35 mL) was stirred at 55° C. for 5.5 h. The mixture was concentrated, diluted with EtOAc, washed with water (2×), dried (MgSO$_4$), and concentrated. The crude material was triturated using hexanes to afford 5-methoxythieno[3,2-b]pyridine-6-carbonitrile (1.56 g, 93% yield) as a brown solid. $^1$H NMR (400 MHz, chloroform-d) δ 8.35 (d, J=0.6 Hz, 1H), 7.96 (d, J=5.5 Hz, 1H), 7.44 (dd, J=5.5, 0.6 Hz, 1H), 4.13 (s, 3H).

Intermediate 1C: 3-Bromo-5-methoxythieno[3,2-b]pyridine-6-carbonitrile

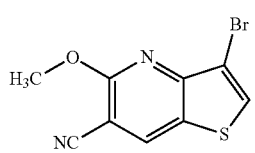

(1C)

A solution of 5-methoxythieno[3,2-b]pyridine-6-carbonitrile (3.15 g, 16.56 mmol) and NBS (3.54 g, 19.87 mmol) in DMF (100 mL) was stirred at 60° C. for 4 h. The mixture was allowed to cool to room temperature followed by the addition of water (20 mL). The solid precipitated product was collected by filtration, washed with water and the triturated with MeOH to afford 3-bromo-5-methoxythieno[3,2-b]pyridine-6-carbonitrile (3.14 g, 71% yield) as a white solid. $^1$H NMR (400 MHz, chloroform-d) 8.35 (s, 1H), 7.95 (s, 1H), 4.21 (s, 3H).

Intermediate 1D: (6-cyano-5-methoxythieno[3,2-b]pyridin-3-yl)boronic acid

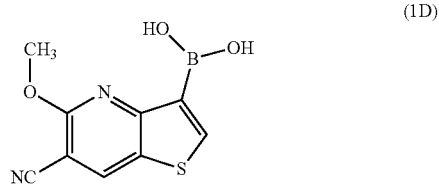 [SMILES: COc1nc2c(B(O)O)csc2cc1C#N]

(1D)

A mixture of 4,4,4',4',5,5,5',5'-octamethyl-2,2'-bi(1,3,2-dioxaborolane) (49.3 g, 194 mmol), 3-bromo-5-methoxythieno[3,2-b]pyridine-6-carbonitrile (47.5 g, 177 mmol), potassium acetate (34.6 g, 353 mmol) and PdCl$_2$(dppf)-CH$_2$Cl$_2$ adduct (11.53 g, 14.12 mmol) in THF (700 mL) was purged with nitrogen for about 10 min and stirred at 60° C. overnight. LC/MS analysis revealed that the reaction was incomplete (about 20% starting material remained). Additional palladium catalyst (2 g) was added and the reaction mixture was stirred at 70° C. (bath temperature) for 5 h.

The mixture was cooled to 15° C. followed by the addition of an aqueous solution (approximately 10%) of N-acetyl-L-cysteine (about 300 mL). The mixture was stirred at room temperature for 1 h. A brown solid precipitated during this time which was isolated by filtration affording crude (6-cyano-5-methoxythieno[3,2-b]pyridin-3-yl)boronic acid (40 g, 97% crude yield) (brown solid). LC/MS (Method A) t$_R$ 0.7 min, m/z 235 [M+H]+.

Intermediate 1E: 3-Hydroxy-5-methoxythieno[3,2-b]pyridine-6-carbonitrile

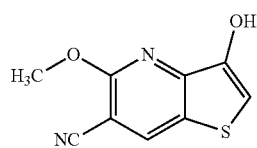

(1E)

To a solution of sodium carbonate (3.12 g, 29.5 mmol) in water (200 mL) was added to a solution of (6-cyano-5-methoxythieno[3,2-b]pyridin-3-yl)boronic acid (2.3 g, 9.83 mmol) in THF (500 mL). To the resulting clear reaction mixture was added 35% hydrogen peroxide (2.87 g, 29.5 mmol) with stirring at room temperature. The reaction mixture was monitored by LC/MS using molecular ions of the starting material and the desired product (starting material and desired product displayed identical retention times in two separate LC/MS systems).

After stirring at room temperature for approximately 1 h, the reaction mixture was diluted with EtOAc. The organic layer was washed sequentially with semi saturated sodium thiosulfate (2×) and brine (1×). All aqueous layers were back extracted with EtOAc. The combined organic phase was dried (MgSO$_4$) and concentrated affording crude product. The crude product was subjected to flash chromatography (silica gel/DCM:MeOH 100:0 to 90:10 gradient) to afford 3-hydroxy-5-methoxythieno[3,2-b]pyridine-6-carbonitrile (1.55 g, 76% yield). LC/MS (Method A) t$_R$ 0.7 min, m/z 207 [M+H]$^+$.

Intermediate 1F: ((2S,3S)-3-ethyl-4,4-difluoro-5-oxopyrrolidin-2-yl)methyl methanesulfonate

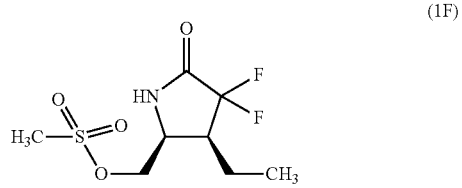 [SMILES: CC[C@H]1[C@@H](COS(C)(=O)=O)NC(=O)C1(F)F]

(1F)

Methanesulfonyl chloride (52.6 µL, 0.675 mmol) and TEA (111 µL, 0.798 mmol) were added sequentially to a stirred solution of (4S,5S)-4-ethyl-3,3-difluoro-5-(hydroxymethyl)pyrrolidin-2-one (110 mg, 0.614 mmol) (see ref. WO 2015/150995) in THF (0.1 mL) and DCM (0.3 mL) at −10° C., stirred for 5 min and allowed to warm to 0° C. The reaction mixture was diluted with methylene chloride and washed with saturated sodium bicarbonate solution. The organic phase was dried (MgSO$_4$) and concentrated to afford crude product. The crude product was subjected to flash chromatography (silica gel/EtOAc-MeOH 100:0 to 90:10 gradient, elutes readily) to afford ((2S,3S)-3-ethyl-4,4-difluoro-5-oxopyrrolidin-2-yl)methyl methanesulfonate (150 mg, 95% yield) as a colorless gum. $^1$H NMR (400 MHz, chloroform-d) δ 7.08 (br s, 1H), 4.49-4.35 (m, 1H), 4.17-3.92 (m, 2H), 3.09 (s, 3H), 2.85-2.55 (m, 1H), 1.90-1.74 (m, 1H), 1.63-1.51 (m, 1H), 1.13 (t, J=7.4 Hz, 3H).

Intermediate 1G: 3-(((2S,3S)-3-ethyl-4,4-difluoro-5-oxopyrrolidin-2-yl)methoxy)-5-methoxythieno[3,2-b]pyridine-6-carbonitrile

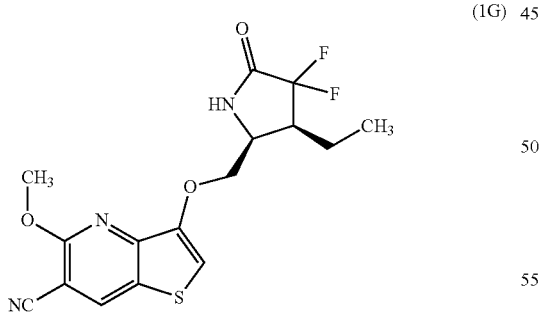

(1G)

A mixture of ((2S,3S)-3-ethyl-4,4-difluoro-5-oxopyrrolidin-2-yl)methyl methanesulfonate (150 mg, 0.583 mmol), 3-hydroxy-5-methoxythieno[3,2-b]pyridine-6-carbonitrile (110 mg, 0.533 mmol) was taken in THF (3 mL) and concentrated to dryness. The residue and anhydrous cesium carbonate (348 mg, 1.067 mmol) were taken in DMF (3 mL) and heated at 90° C. for 10 min. The reaction mixture was diluted with EtOAc, washed with saturated sodium bicarbonate, dried (MgSO$_4$) and concentrated. The crude product was subjected to flash chromatography (silica gel/hexane-EtOAc 100:0 to 0:100 gradient) to afford 3-(((2S,3S)-3-ethyl-4,4-difluoro-5-oxopyrrolidin-2-yl)methoxy)-5-methoxythieno[3,2-b]pyridine-6-carbonitrile (170 mg, 87% yield) as a white solid. LC/MS (Method A) t$_R$ 0.88 min, m/z 368 [M+H]$^+$.

Example 1

Hydrogen peroxide (35%, 135 mg, 1.388 mmol) was added to a stirred mixture of 3-(((2S,3S)-3-ethyl-4,4-difluoro-5-oxopyrrolidin-2-yl)methoxy)-5-methoxythieno[3,2-b]pyridine-6-carbonitrile (170 mg, 0.463 mmol) and potassium carbonate (192 mg, 1.388 mmol) in DMSO (3 mL) and stirred at room temperature for 1 h. The reaction mixture was diluted with EtOAc, washed with saturated sodium bicarbonate, dried (MgSO$_4$) and concentrated. The crude product was subjected to preparative HPLC (ODS column/water-MeOH-TFA 90:10:0.05 to 10:90:0.05 gradient) to afford a white solid. The solid material was dissolved in DCM and a few drops of MeOH and washed with saturated NaHCO$_3$. The organic layer was dried (MgSO$_4$) and concentrated to afford the product which was recrystallized from MeOH to afford 3-(((2S,3S)-3-ethyl-4,4-difluoro-5-oxopyrrolidin-2-yl)methoxy)-5-methoxythieno[3,2-b]pyridine-6-carboxamide (82 mg, 46% yield) as a white solid (concentration of mother liquor afforded 40 mg of a less pure batch). LC/MS (Method A) t$_R$ 0.72 min, m/z 386 [M+H]$^+$. $^1$H NMR (400 MHz, methanol-d$_4$+CDCl$_3$) δ 8.86 (s, 1H), 7.01 (s, 1H), 4.31 (dd, J=8.8, 3.5 Hz, 1H), 4.22-4.07 (m, 5H), 2.92-2.56 (m, 1H), 1.96-1.51 (m, 2H), 1.14 (t, J=7.4 Hz, 3H).

Example 2

3-(((2S,3S,4S)-3-Ethyl-4-fluoro-5-oxopyrrolidin-2-yl)methoxy)-5-methoxythieno[3,2-b]pyridine-6-carboxamide

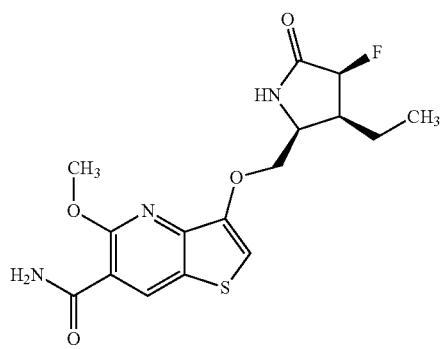

(2)

Intermediate 2A: 3-(((2S,3S,4S)-3-ethyl-4-fluoro-5-oxopyrrolidin-2-yl)methoxy)-5-methoxythieno[3,2-b]pyridine-6-carbonitrile

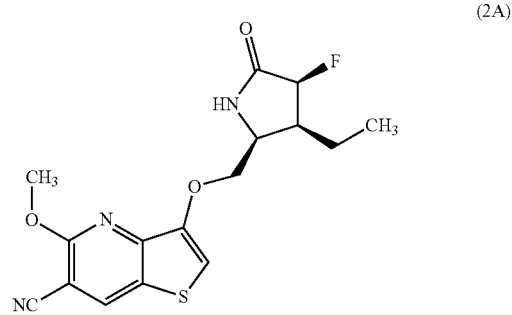 [SMILES: CC[C@@H]1[C@H](F)C(=O)N[C@@H]1COc1csc2cc(C#N)c(OC)nc12]

(2A)

Mesyl chloride (148 µL, 1.904 mmol) and TEA (314 µL, 2.250 mmol) were added sequentially to a stirred solution of (3S,4S,5S)-4-ethyl-3-fluoro-5-(hydroxymethyl) pyrrolidin-2-one (279 mg, 1.731 mmol) in DCM (5 mL) at −10° C., stirred for 5 min and then allowed to warm to 0° C. The reaction mixture was diluted with DCM and washed with saturated sodium bicarbonate solution. The organic phase was dried (MgSO$_4$) and concentrated to afford crude product.

The crude product and 3-hydroxy-5-methoxythieno[3,2-b]pyridine-6-carbonitrile (321 mg, 1.558 mmol) were taken in DMF (5 mL) followed by the addition of cesium carbonate (1128 mg, 3.46 mmol). The mixture was stirred at 60° C. for 2 h. The reaction mixture was diluted with EtOAc, washed with saturated sodium bicarbonate, dried (MgSO$_4$) and concentrated. The crude product was subjected to flash chromatography (silica gel/hexane-EtOAc 100:0 to 0:100 gradient) to afford 3-(((2S,3S,4S)-3-ethyl-4-fluoro-5-oxopyrrolidin-2-yl)methoxy)-5-methoxythieno[3,2-b]pyridine-6-carbonitrile (200 mg, 33% yield). LC/MS (Method B) $t_R$ 0.86 min, m/z 350 [M+H]+.

Example 2: 3-(((2S,3S,4S)-3-Ethyl-4-fluoro-5-oxopyrrolidin-2-yl)methoxy)-5-methoxythieno[3,2-b]pyridine-6-carboxamide Hydrogen peroxide (35%, 167 mg, 1.717 mmol) was added to a stirred mixture of 3-(((2S,3S,4S)-3-ethyl-4-fluoro-5-oxopyrrolidin-2-yl)methoxy)-5-methoxythieno[3,2-b]pyridine-6-carbonitrile (200 mg, 0.572 mmol) and potassium carbonate (237 mg, 1.717 mmol) in DMSO (3 mL) and the mixture was stirred at room temperature for 1 h. The reaction mixture was diluted with EtOAc, washed with saturated sodium bicarbonate, dried (MgSO$_4$) and concentrated. The crude product was purified by preparative HPLC (ODS column/water-MeOH-TFA 90:10:0.1 to 10:90:0.1 gradient) to afford white solid. The solid material was dissolved in DCM+a few drops of MeOH and washed with saturated NaHCO$_3$. The organic layer was dried (MgSO$_4$) and concentrated to afford the product which was triturated with MeOH to afford 3-(((2S,3S,4S)-3-ethyl-4-fluoro-5-oxopyrrolidin-2-yl)methoxy)-5-methoxythieno[3,2-b]pyridine-6-carboxamide (125 mg, 58% yield) as a white solid. $^1$H NMR (400 MHz, methanol-d$_4$) δ 8.78 (s, 1H), 8.73-8.71 (m, 1H), 7.24 (s, 1H), 4.84 (dd, J=53.1, 5.6 Hz, 1H, overlaps with water peak), 4.54-4.29 (m, 1H), 4.23-4.15 (m, 5H), 2.76-2.49 (m, 1H), 1.83-1.62 (m, 2H), 1.12 (t, J=7.3 Hz, 3H). $^{19}$F NMR (376 MHz, methanol-d$_4$) δ −200.62 (s, 1F). LC/MS (Method B) $t_R$ 0.7 min, m/z 368 [M+H]$^+$.

Example 3

(S)-5-Methoxy-3-((5-oxopyrrolidin-2-yl)methoxy)thieno[2,3-b]pyridine-6-carboxamide (3)

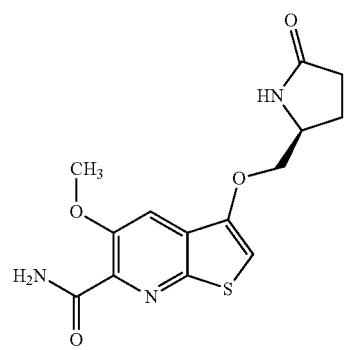

Intermediate 3A: Methyl 5-chloro-6-cyano-2-((2-methoxy-2-oxoethyl)thio)nicotinate

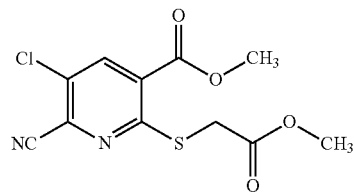

(3A)

Methyl 2,5-dichloro-6-cyanonicotinate (0.495 g) was prepared from 2,5-dichloronicotinate as described in PCT Intl Appl., 2011130342.

LiHMDS (1 M in THF) (1.35 mL, 1.35 mmol) was added at 0° C. to a solution of methyl 2-mercaptoacetate (0.12 mL, 1.29 mmol) in THF (1 mL) and stirred for 5 minutes. Then, a solution of methyl 2,5-dichloro-6-cyanonicotinate (0.297 g, 1.29 mmol) in THF (5 mL) was added and stirred at 0° C. for 30 minutes. The reaction mixture was warmed to room temperature. The reaction was quenched with water. The mixture was diluted with EtOAc. The organic phase was washed with saturated NH$_4$Cl, dried (MgSO$_4$), and concentrated. The crude was purified using flash chromatography (silica gel/hexanes/ethyl acetate 100:0 to 0:100 gradient) to afford methyl 5-chloro-6-cyano-2-((2-methoxy-2-oxoethyl)thio)nicotinate (0.258 g, 66.7% yield) as a yellow solid. $^1$H NMR (400 MHz, chloroform-d) δ 8.36 (s, 1H), 4.00 (s, 3H), 3.88 (s, 2H), 3.80 (s, 3H).

Intermediate 3B: Methyl 5-chloro-6-cyano-3-hydroxythieno[2,3-b]pyridine-2-carboxylate

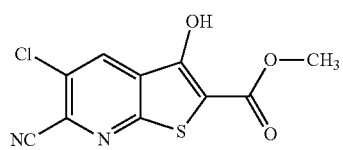

(3B)

A solution of methyl 5-chloro-6-cyano-2-((2-methoxy-2-oxoethyl)thio)nicotinate (0.258 g, 0.86 mmol) and DBU (0.142 mL, 0.94 mmol) in toluene (6 mL) was stirred at room temperature overnight. HCl (1 N) was added and stirred for 5 minutes. The mixture was extracted with EtOAc, dried (MgSO$_4$), and concentrated. The crude product was purified using flash chromatography (silica gel/hexanes-ethyl acetate 100:0 to 0:100 gradient) to afford methyl 5-chloro-6-cyano-3-hydroxythieno[2,3-b]pyridine-2-carboxylate (0.181 g, 79% yield) as an orange solid. LC MS (Method A) $t_R$ 0.72, m/z 267 [M−H]. $^1$H NMR (400 MHz, chloroform-d) δ 10.08 (s, 1H), 8.35 (s, 1H), 4.02 (s, 3H).

Intermediate 3C: Methyl 6-carbamoyl-5-chloro-3-hydroxythieno[2,3-b]pyridine-2-carboxylate

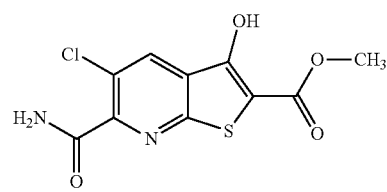

(3C)

A solution of methyl 5-chloro-6-cyano-3-hydroxythieno[2,3-b]pyridine-2-carboxylate (0.602 g, 2.24 mmol) in sulfuric acid (3 mL, 56.3 mmol) was stirred at 60° C. for 2 hours, cooled to 0° C. followed by the addition of 1N HCl. The resulting precipitated solid was collected by filtration and washed with water to afford methyl 6-carbamoyl-5-chloro-3-hydroxythieno[2,3-b]pyridine-2-carboxylate (0.625 g, 97% yield) as a brown solid. LC/MS (Method B) $t_R$ 0.69, m/z 287 [M−H]+.

Intermediate 3D: 5-Chloro-3-hydroxythieno[2,3-b]pyridine-6-carboxamide

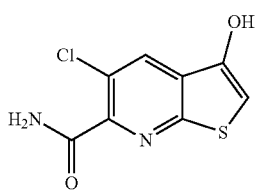

(3D)

To a stirred solution of potassium tert-butoxide (2.446 g, 21.8 mmol) in DMSO (15 mL) was added methyl 6-carbamoyl-5-chloro-3-hydroxythieno[2,3-b]pyridine-2-carboxylate (0.625 g, 2.18 mmol) at room temperature. After 30 minutes at room temperature, the reaction mixture was heated at 80° C. for 2.5 hours (*BMCL* 22 (2012) 5031-5034). The mixture was diluted with EtOAc, washed with 1N HCl, water, dried (MgSO4), and concentrated. The crude product was dissolved in pyridine (10 mL) and stirred at 80° C. for 15 minutes. The mixture was concentrated, diluted with EtOAc, washed with 1N HCl, water, dried (MgSO4), and concentrated. The crude material was purified using flash chromatography (silica gel/hexanes-ethyl acetate-methanol 100:0:0 to 0:90:10 gradient) to afford 5-chloro-3-hydroxythieno[2,3-b]pyridine-6-carboxamide (0.369 g, 74% yield) as a brown solid. LC/MS (Method B) $t_R$ 0.54, m/z 229 [M+H]+. 1H NMR (400 MHz, methanol-d4) δ 8.19 (s, 1H), 6.66 (s, 1H).

Intermediate 3E: (S)-5-Chloro-3-((5-oxopyrrolidin-2-yl)methoxy)thieno[2,3-b]pyridine-6-carboxamide

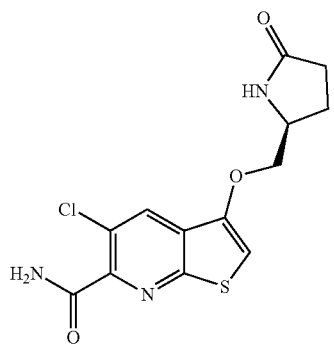

(3E)

A mixture of 5-chloro-3-hydroxythieno[2,3-b]pyridine-6-carboxamide (0.1 g, 0.44 mmol) (S)-(5-oxopyrrolidin-2-yl)methyl 4-methylbenzenesulfonate (0.118 g, 0.44 mmol) and cesium carbonate (0.285 g, 0.88 mmol) in DMF (2 mL) was stirred at 65° C. for 1.5 h. The mixture was cooled to room temperature and filtered. The crude material was purified using preparative HPLC (Phen. Luna Axia C18 5µ; 30×100 mm column; detection at 220 nm; flow rate 40 mL/min; continuous gradient from 0% B to 100% B over 10 min, 2 min hold at 100% B, where A=10:90:0.1 MeOH—H2O-TFA and B=90:10:0.1 MeOH—H2O-TFA) to afford (S)-5-chloro-3-((5-oxopyrrolidin-2-yl)methoxy) thieno[2,3-b]pyridine-6-carboxamide (21 mg, 14% yield) as a light brown solid. LC/MS (Method B) $t_R$ 0.58, m/z 326 [M+H]+. 1H NMR (400 MHz, DMSO-d6) δ 8.42 (s, 1H), 8.12 (br. s., 1H), 8.08 (s, 1H), 7.78 (br. s., 1H), 7.10 (s, 1H), 4.22 (dd, J=9.0, 3.4 Hz, 1H), 4.03-3.90 (m, 2H), 2.37-2.12 (m, 3H), 1.87-1.78 (m, 1H).

Example 3

A solution of (S)-5-chloro-3-((5-oxopyrrolidin-2-yl)methoxy)thieno[2,3-b]pyridine-6-carboxamide (12 mg, 0.04 mmol), copper(I) iodide (0.702 mg, 3.68 µmol) and sodium methoxide (25% in MeOH) (0.13 mL, 0.55 mmol) was stirred at 65° C. for 1 hour, cooled to room temperature and then filtered. The crude product was purified using preparative HPLC (Phen. Luna Axia C18 5µ; 21.2×100 mm column; detection at 220 nm; flow rate=40 mL/min; continuous gradient from 0% B to 100% B over 10 min+2 min hold at 100% B, where A=10:90:0.1 MeOH—H2O-TFA and B=90:10:0.1 MeOH—H2O-TFA) to afford (S)-5-methoxy-3-((5-oxopyrrolidin-2-yl)methoxy)thieno[2,3-b]pyridine-6-carboxamide (4.1 mg, 33.3% yield) as a yellow solid. LC/MS (Method A) $t_R$ 0.48, m/z 322 [M+H]+.

Example 4

3-(((2S,3S,4S)-3-ethyl-4-fluoro-5-oxopyrrolidin-2-yl)methoxy)-5-methoxybenzo[b]thiophene-6-carboxamide

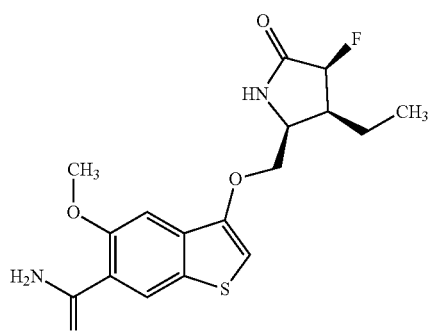

(4)

Intermediate 4A:
6-Bromo-5-methoxybenzo[b]thiophene

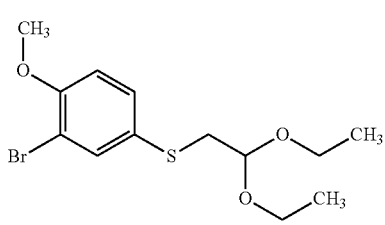

(4A)

A mixture of 3-bromo-4-methoxythiophenol (1.08 g, 4.93 mmol), 2-bromo-1,1-diethoxyethane (1.001 g, 5.08 mmol) and K$_2$CO$_3$ (0.783 g, 5.67 mmol) in DMF (10 mL) was stirred at 110° C. for 7 hours. The mixture was allowed to come to room temperature, diluted with DCM and washed with 10% LiCl. The organic layer was then dried over Na$_2$SO$_4$ and concentrated to afford (3-bromo-4-methoxyphenyl)(2,2-diethoxyethyl)sulfane (1.6 g, 4.77 mmol, 97% yield).

Intermediate 4B: 5-Methoxybenzo[b]thiophene-6-carbonitrile

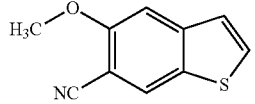

(4B)

A solution of (3-bromo-4-methoxyphenyl)(2,2-diethoxyethyl)sulfane (1.6 g, 4.77 mmol) in chlorobenzene (2 mL) was added to a preheated stirred mixture of chlorobenzene (8 mL) and PPA (0.534 mL, 4.93 mmol) at 120° C. The mixture was stirred at 120° C. for 6 h, allowed to cool to room temperature, diluted with EtOAc, and washed with water. The organic layer was then concentrated and crude product was subjected to flash chromatography (silica gel/hexanes-EtOAc 100:0 to 0:100 gradient) to afford a mixture of the two regioisomers (535 mg).

The above mixture, zinc cyanide (700 mg, 5.96 mmol) and palladium tetrakis triphenylphosphine (197 mg, 0.170 mmol) were taken in DMF (9 mL), purged with nitrogen and stirred at 120° C. for 3 h. The reaction mixture was diluted with EtOAc, washed with saturated NH$_4$Cl and brine, dried (MgSO$_4$) and concentrated. The crude product was subjected to flash chromatography (silica gel/hexane-EtOAc 100:0 to 30:70 gradient) to afford a more pure mixture of the two regioisomers. The material was subjected to SFC (Cellulose-4 5 µm column/CO$_2$-MeOH 85:15 at 35° C.) to afford 5-methoxybenzo[b]thiophene-4-carbonitrile as the faster eluting isomer and the product 5-methoxybenzo[b]thiophene-6-carbonitrile (225 mg) as the slower eluting isomer. $^1$H NMR (400 MHz, chloroform-d) δ 8.09 (s, 1H), 7.71-7.72 (d, 1H), 7.34 (s, 1H), 7.32-7.33 (d, J=5.2 Hz, 1H), 4.01 (s, 3H).

Intermediate 4C: 3-Bromo-5-methoxybenzo[b]thiophene-6-carbonitrile

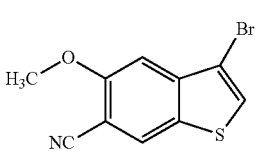

(4C)

A mixture of 5-methoxybenzo[b]thiophene-6-carbonitrile (225 mg, 1.189 mmol) and NBS (275 mg, 1.546 mmol) in DMF (5 mL) were stirred at 60° C. for 3 h, diluted with DCM and washed sequentially with 10% LiCl and brine. The organic layer was then dried over Na$_2$SO$_4$, concentrated and the residue was triturated with MeOH to afford 3-bromo-5-methoxybenzo[b]thiophene-6-carbonitrile (245 mg, 7% yield). $^1$H NMR (400 MHz, chloroform-d) δ 8.06 (s, 1H), 7.69 (s, 1H), 7.30 (s, 1H), 4.09-4.05 (m, 4H).

Intermediate 4D: 3-Hydroxy-5-methoxybenzo[b]thiophene-6-carbonitrile

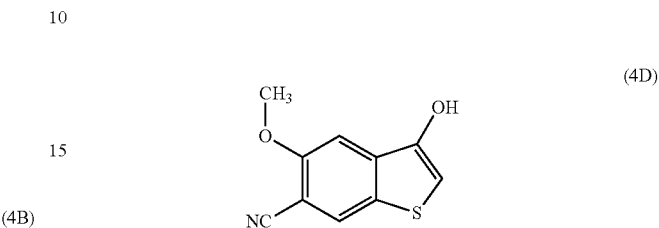

(4D)

To the stirred solution of 3-bromo-5-methoxybenzo[b]thiophene-6-carbonitrile (242 mg, 0.903 mmol) in 1,4-dioxane (8 mL) was added 4,4,4',4',5,5,5',5'-octamethyl-2,2'-bi(1,3,2-dioxaborolane) (248 mg, 0.975 mmol) and potassium acetate (186 mg, 1.895 mmol). The mixture was purged with N$_2$, then PdCl$_2$(dppf)-CH$_2$Cl$_2$ adduct (73.7 mg, 0.090 mmol) was added. The mixture was stirred at 60° C. for 24 h. The mixture was diluted with EtOAc, filtered through celite and the filtrated was concentrated. The residue was stirred with mercaptopropyl bound silica in THF (5 mL) at 40° C. for 24 h. The mixture was filtered through celite. The filtrate was then treated sequentially with sodium bicarbonate (379 mg, 4.51 mmol) in water (3 mL) and 35% hydrogen peroxide (0.138 mL). The reaction mixture was stirred at room temperature for 45 min, diluted with EtOAc and washed with water and brine. The organic layer was then dried over Na$_2$SO$_4$, concentrated and the residue was subjected to flash chromatography (silica gel/hexane-EtOAc 100:0 to 0:100 gradient) to afford 3-hydroxy-5-methoxybenzo[b]thiophene-6-carbonitrile (10 mg, 0.049 mmol, 5.4% yield).

Example 4

A mixture of ((2S,3S,4S)-3-ethyl-4-fluoro-5-oxopyrrolidin-2-yl)methyl 4-methylbenzenesulfonate (24.43 mg, 0.077 mmol), 3-hydroxy-5-methoxybenzo[b]thiophene-6-carbonitrile (15 mg, 0.073 mmol) and Cs$_2$CO$_3$ (50 mg, 0.153 mmol) in DMF (2 mL) was stirred at 60° C. for 5 hours. The reaction mixture was diluted with EtOAc and washed with 10% LiCl. The organic layer was dried over Na$_2$SO$_4$ and then concentrated. The residue was dissolved into DMSO (1.5 mL). K$_2$CO$_3$ (25.3 mg, 0.183 mmol) and 35% hydrogen peroxide (0.112 mL, 1.096 mmol) were added. The mixture was allowed to stir at 48° C. for 12 h. The mixture was filtered and the filtrate was subjected to preparative HPLC (C18 column/water-acetonitrile with 10 mM ammonium acetate 90:10 to 10:90 gradient) to afford 3-(((2S,3S,4S)-3-ethyl-4-fluoro-5-oxopyrrolidin-2-yl)methoxy)-5-methoxybenzo[b]thiophene-6-carboxamide (4.2 mg). LC/MS (Method C) t$_R$ 1.19, m/z 367 [M+H]$^+$. $^1$H NMR (500 MHz, DMSO-d$_6$) δ 8.86 (br s, 1H), 8.24 (s, 1H), 7.77 (br s, 1H), 7.55 (br s, 1H), 7.46 (s, 1H), 6.98 (s, 1H), 4.87 (dd, J=53.4, 5.5 Hz, 1H), 4.23-4.15 (m, 1H), 4.04 (br s, 1H), 3.93 (s, 3H), 3.52 (br d, J=7.6 Hz, 1H), 1.72-1.48 (m, 2H), 1.00 (br t, J=7.6 Hz, 3H).

The Examples in Table 1 were prepared using the methods outlined for Examples 1-4 using the appropriate starting materials.

TABLE 1

| Ex. No. | Structure | HPLC $R_T$ (min) | HPLC cond. | LCMS |
|---|---|---|---|---|
| 5 | 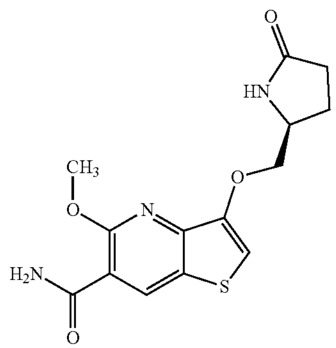 [SMILES: COc1nc2c(OC[C@@H]3CCC(=O)N3)csc2cc1C(N)=O] | 0.57 | Method B | 322.0 |
| 6 | 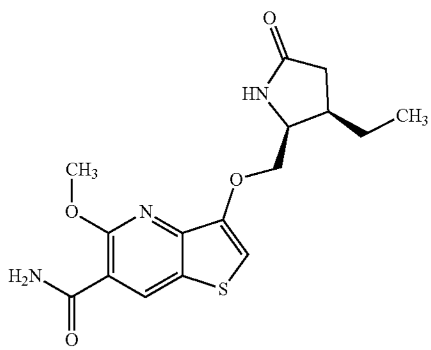 [SMILES: CC[C@@H]1CC(=O)N[C@@H]1COc1csc2cc(C(N)=O)c(OC)nc12] | 1.09 | Method C | 350.0 |
| 7 | (racemic) | 0.91 | Method C | 338.0 |
| 8 | 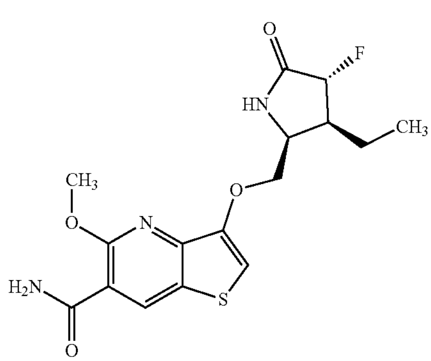 [SMILES: CC[C@H]1[C@@H](COc2csc3cc(C(N)=O)c(OC)nc23)NC(=O)[C@@H]1F] | 1.15 | Method C | 368.0 |

TABLE 1-continued

| Ex. No. | Structure | HPLC R_T (min) | HPLC cond. | LCMS |
|---|---|---|---|---|
| 9 | 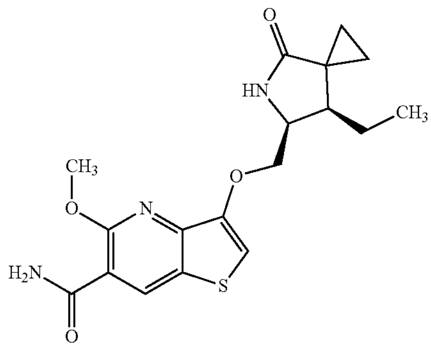 [SMILES: CC[C@H]1[C@@H](COc2csc3cc(C(N)=O)c(OC)nc23)NC(=O)C12CC2] | 1.15 | Method C | 348.0 |
| 10 | 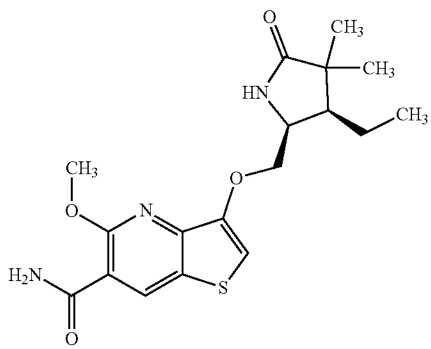 [SMILES: CC[C@H]1[C@@H](COc2csc3cc(C(N)=O)c(OC)nc23)NC(=O)C1(C)C] | 1.01 | Method C | 350.0 |
| 11 | 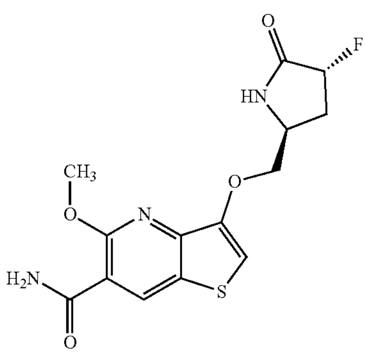 [SMILES: COc1nc2c(OC[C@@H]3C[C@@H](F)C(=O)N3)csc2cc1C(N)=O] | 0.86 | Method C | 340.0 |
| 12 | 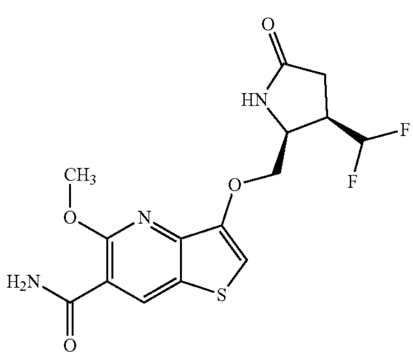 [SMILES: COc1nc2c(OC[C@H]3NC(=O)C[C@H]3C(F)F)csc2cc1C(N)=O] | 0.64 | Method B | 372.0 |

TABLE 1-continued

| Ex. No. | Structure | HPLC R$_T$ (min) | HPLC cond. | LCMS |
|---|---|---|---|---|
| 13 | Diastereomer 1 | 0.91 | Method C | 336.0 |
| 14 | Diastereomer 2 | 0.90 | Method C | 336.0 |
| 15 | Diastereomer 1 | 1.22 | Method C | 350.0 |
| 16 | Diastereomer 2 | 1.26 | Method C | 350.0 |

TABLE 1-continued

| Ex. No. | Structure | HPLC R_T (min) | HPLC cond. | LCMS |
|---|---|---|---|---|
| 17 | 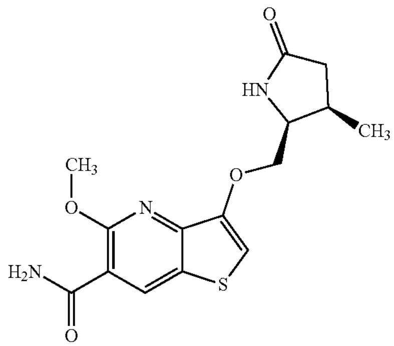 [SMILES: COc1nc2c(OC[C@H]3NC(=O)C[C@H]3C)csc2cc1C(N)=O] | 0.98 | Method C | 336.0 |
| 18 | 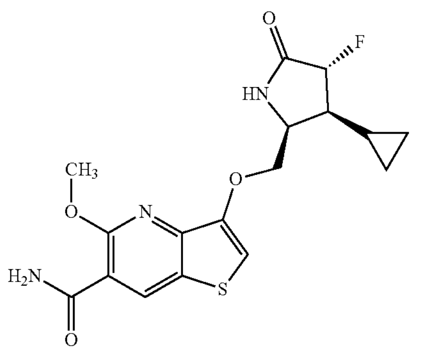 [SMILES: COc1nc2c(OC[C@H]3NC(=O)[C@H](F)[C@H]3C3CC3)csc2cc1C(N)=O] | 0.73 | Method B | 380.0 |
| 19 | 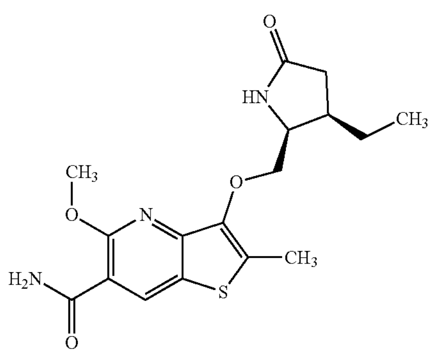 [SMILES: CC[C@@H]1CC(=O)N[C@@H]1COc1c(C)sc2cc(C(N)=O)c(OC)nc12] | 1.38 | Method C | 364.0 |
| 20 | 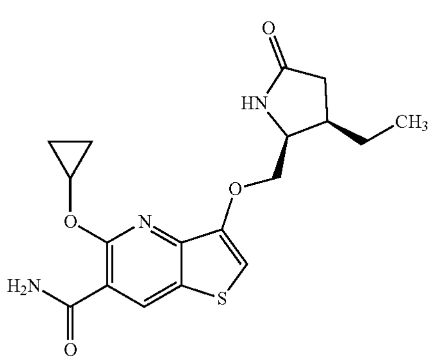 [SMILES: CC[C@@H]1CC(=O)N[C@@H]1COc1csc2cc(C(N)=O)c(OC3CC3)nc12] | 1.43 | Method C | 376.0 |

TABLE 1-continued

| Ex. No. | Structure | HPLC R$_T$ (min) | HPLC cond. | LCMS |
|---|---|---|---|---|
| 21 | 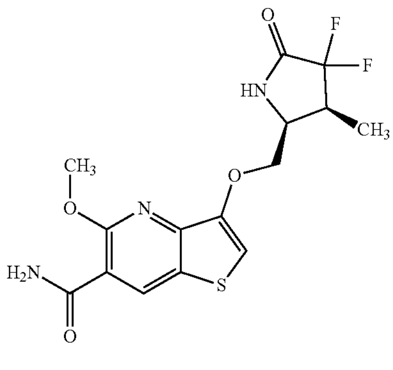 [SMILES: COc1nc2c(OC[C@H]3NC(=O)C(F)(F)[C@H]3C)csc2cc1C(N)=O] | 1.13 | Method C | 372.0 |
| 22 | 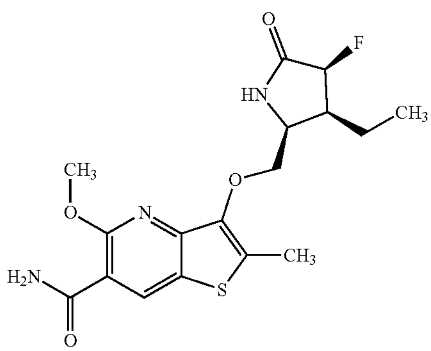 [SMILES: CC[C@@H]1[C@H](F)C(=O)N[C@@H]1COc1c(C)sc2cc(C(N)=O)c(OC)nc12] | 1.31 | Method C | 382.0 |
| 23 | 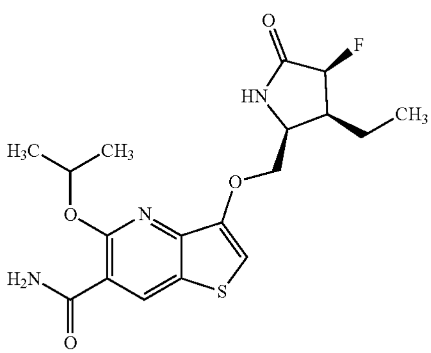 [SMILES: CC[C@@H]1[C@H](F)C(=O)N[C@@H]1COc1csc2cc(C(N)=O)c(OC(C)C)nc12] | 1.36 | Method C | 396.0 |
| 24 | 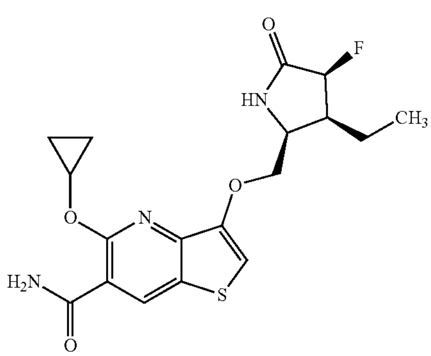 [SMILES: CC[C@@H]1[C@H](F)C(=O)N[C@@H]1COc1csc2cc(C(N)=O)c(OC3CC3)nc12] | 1.30 | Method C | 394.0 |

TABLE 1-continued

| Ex. No. | Structure | HPLC R_T (min) | HPLC cond. | LCMS |
|---|---|---|---|---|
| 25 | 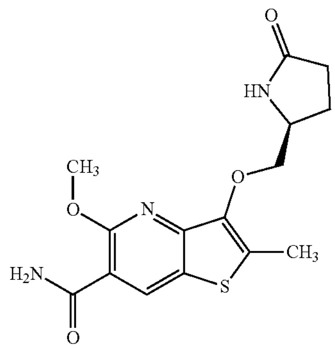 [SMILES: COc1nc2c(OC[C@@H]3CCC(=O)N3)c(C)sc2cc1C(N)=O] | 1.00 | Method C | 336.0 |
| 26 | 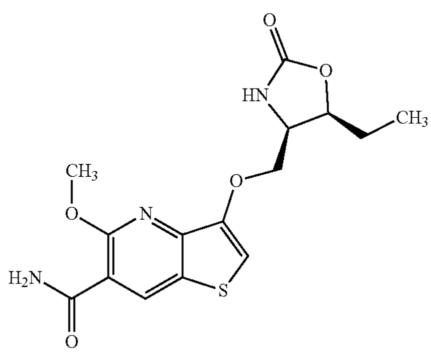 [SMILES: CC[C@@H]1OC(=O)N[C@@H]1COc1csc2cc(C(N)=O)c(OC)nc12] | 0.68 | Method C | 352.0 |
| 27 | 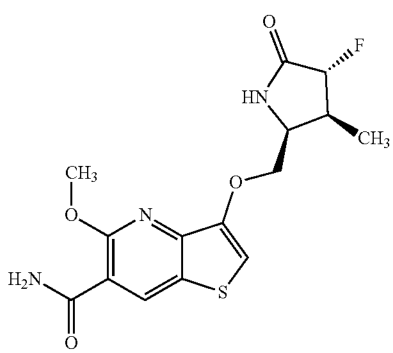 [SMILES: COc1nc2c(OC[C@H]3NC(=O)[C@H](F)[C@H]3C)csc2cc1C(N)=O] | 0.67 | Method B | 354.0 |
| 28 | 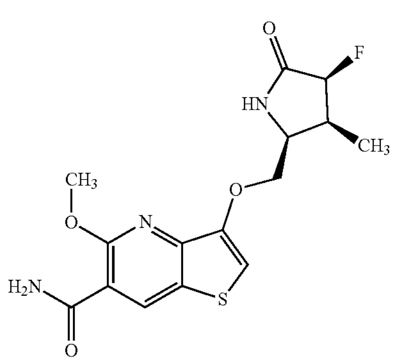 [SMILES: COc1nc2c(OC[C@H]3NC(=O)[C@@H](F)[C@H]3C)csc2cc1C(N)=O] | 0.66 | Method B | 354.0 |

TABLE 1-continued

| Ex. No. | Structure | HPLC R$_T$ (min) | HPLC cond. | LCMS |
|---|---|---|---|---|
| 29 | (structure) | 1.13 | Method C | 349.0 |

BIOLOGICAL ASSAYS

The pharmacological properties of the compounds of this invention may be confirmed by a number of biological assays. The exemplified biological assays, which follow, have been carried out with compounds of the invention.

IRAK4 Inhibition Assay

The assays were performed in U-bottom 384-well plates. The final assay volume was 30 µL prepared from 15 µL additions of enzyme and substrates (fluoresceinated peptide and ATP) and test compounds in assay buffer (20 mM HEPES pH 7.2, 10 mM MgCl$_2$, 0.015% Brij 35 and 4 mM DTT). The reaction was initiated by the combination of IRAK4 with substrates and test compounds. The reaction mixture was incubated at room temperature for 60 min. and terminated by adding 45 µL of 35 mM EDTA to each sample. The reaction mixture was analyzed on the Caliper LAB-CHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentrations of reagents in the assays are ATP, 500 µM; FL-IPTSPITT-TYFFFKKK peptide 1.5 µM; IRAK4, 0.6 nM; and DMSO, 1.6%.

Caco-2 Permeability Assay

Thirteen to 27 days prior to assay, Caco-2 cells were seeded onto collagen-coated polycarbonate filter membranes in 24-well transwell plates at a density of 1.45×10$^5$ cells/cm$^2$, approximately 4.8×10$^4$ cells per well. The cells were grown in a culture medium consisting of DMEM supplemented with 10% fetal bovine serum, 10 mM HEPES, 1% nonessential amino acids, 2 mM L-glutamine, 100 U/mL penicillin-G, and 100 µg/mL streptomycin. The culture medium was replaced every 3 days and the cells were maintained at 37° C. in a 95% relative humidity and 5% CO$_2$ atmosphere. The cells were evaluated for tight junction formation just prior to assay. The test compound was solubilized to 10 mM in 100% DMSO and diluted to 3 µM in assay buffer. Permeability studies were initiated by adding 200 µL assay buffer plus/minus compound to the apical transwell compartment and 600 µL assay buffer plus/minus compound to the basolateral compartment of the 24-well transwell low-binding cluster plate. For apical-to-basolateral (A to B) permeability (absorptive direction), buffer containing compound was placed in the apical compartment (donor-wells), while buffer alone was placed in the corresponding basolateral compartments (receiverwells). For basolateral-to-apical (B to A) permeability (secretive direction), buffer containing compound was placed in the basolateral compartment (donor wells), while buffer alone was placed in the corresponding apical compartments (receiver wells). Transwells were then incubated for 2 hours at 37° C. in a 95% relative humidity and 5% CO$_2$ atmosphere with gentle agitation. Following incubation, 100 µL was removed from each apical and basolateral compartment and transferred to 96-well low binding plates that had been previously loaded with 100 µL/well of acetonitrile containing 250 nM propranolol, 250 nM diclofenac, and 500 nM tolbutamide as internal standards. The samples were subsequently analyzed by LC-MS/MS to determine concentrations of compound.

IRAK4 Whole Blood Assay

Human whole blood containing the anti-coagulant ACD-A was plated in 384-well plate (25 µL/well) and incubated with compounds for 60 minutes at 37° C. in a 5% CO$_2$ incubator. The blood was stimulated with a TLR2 agonist, 10 µg/mL final concentration of lipoteichoic acid (Invivogen, San Diego, Calif.) in 25 µL RPMI (Gibco) for 5 hours in a 5% CO$_2$ incubator. At the end of the incubation, plates were centrifuged at 2300 rpm for 5 minutes. Supernatants were harvested and analyzed for IL-6 levels by Flow Cytometry beads assay (BD Biosciences, San Jose, Calif.).

PBMC TLR2 Induced IL-6 Assay.

Peripheral blood mononuclear cells (PBMCs) were isolated from human blood containing the anti-coagulant EDTA (2.5 mM) by centrifugation over a Ficoll gradient. PBMCs (250000 cells/well) were cultured in assay media (RPMI with 10% heat inactivated FCS) with compounds for 30 minutes at 37° C. in a 5% CO$_2$ incubator. Following pretreatment with compounds, cells were stimulated for 5 hours with 10 µg/mL lipoteichoic acid (Invivogen, San Diego, Calif.), a TLR2 agonist. At the end of the culture, plates were centrifuged at 1800 rpm for 10 minutes to pellet the cells. Supernatants were harvested and analyzed for IL-6 levels by ELISA (BD Biosciences, San Jose, Calif.).

The table below lists the IRAK4 IC$_{50}$ values, the Whole Blood EC$_{50}$ values, and Caco-2 Permeability values for the following examples of this invention measured in the IRAK4 Inhibition Assay, IRAK4 Whole Blood Assay and the Caco-2 Permeability assay.

The compounds of the present invention, as exemplified by the following examples, showed IRAK IC$_{50}$ inhibition values of less than 0.6 µM.

TABLE 2

| | IRAK4 Inhibition Data | | |
|---|---|---|---|
| Ex. No. | IRAK4 IC$_{50}$ (μM) | Whole Blood EC$_{50}$ (μM) | Caco-2 Permeability (nm/s) |
| 1 | 0.0006 | 0.058 | 102 |
| 2 | 0.0012 | 0.205 | 73 |
| 3 | 0.5578 | — | — |
| 4 | 0.0004 | 0.153 | 85 |
| 5 | 0.0203 | 2.007 | — |
| 6 | 0.0010 | 3.211 | 81 |
| 7 | 0.6151 | — | — |
| 8 | 0.0007 | 0.092 | 42 |
| 9 | 0.1296 | — | — |
| 10 | 0.5953 | — | — |
| 11 | 0.0040 | 0.473 | — |
| 12 | 0.0025 | 0.261 | — |
| 13 | 0.0362 | — | — |
| 14 | 0.4593 | — | — |
| 15 | 0.0634 | — | — |
| 16 | 0.0981 | — | — |
| 17 | 0.0060 | 0.893 | — |
| 18 | 0.0028 | 0.962 | — |
| 19 | 0.0106 | 3.299 | 225 |
| 20 | 0.0191 | 0.473 | — |
| 21 | 0.0013 | 0.127 | 136 |
| 22 | 0.0336 | — | — |
| 23 | 0.0014 | 0.189 | 184 |
| 24 | 0.0202 | >10 | — |
| 25 | 0.1279 | — | — |
| 26 | 0.0068 | — | 35 |
| 27 | 0.0011 | 0.058 | 59 |
| 28 | 0.0133 | 0.736 | 58 |
| 29 | 0.0009 | 0.363 | — |

What is claimed is:

1. A compound of Formula (I)

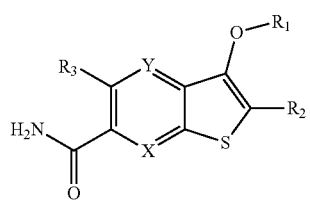

or a salt thereof, wherein:

X is CR$_4$ or N;

Y is CR$_5$ or N; provided that only one of X and Y is N;

R$_1$ is:

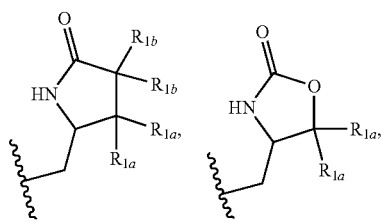

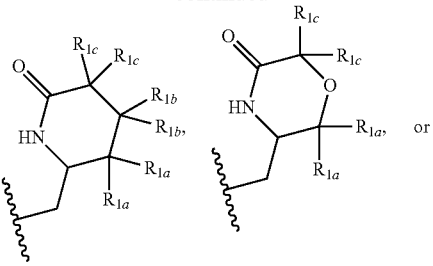

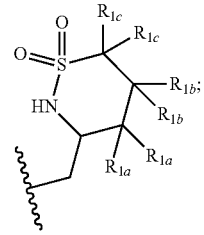

each R$_{1a}$ is independently H, —OH, F, C$_{1-3}$ alkyl, C$_{1-3}$ fluoroalkyl, C$_{1-3}$ alkoxy, C$_{1-3}$ fluoroalkoxy, or C$_{3-6}$ cycloalkyl; or two R$_{1a}$ along with the carbon atom to which they are attached, can form a 3- to 4-membered spirocycloalkyl ring;

each R$_{1b}$ is independently H, —OH, F, C$_{1-3}$ alkyl, C$_{1-3}$ fluoroalkyl, C$_{1-3}$ alkoxy, C$_{1-3}$ fluoroalkoxy, or C$_{3-6}$ cycloalkyl; or two R$_{1b}$ along with the carbon atom to which they are attached, can form a 3-to 4-membered spirocycloalkyl ring;

each R$_{1c}$ is independently H, —OH, F, C$_{1-3}$ alkyl, C$_{1-3}$ fluoroalkyl, C$_{1-3}$ alkoxy, C$_{1-3}$ fluoroalkoxy, or C$_{3-6}$ cycloalkyl; or two R$_{1c}$ along with the carbon atom to which they are attached, can form a 3- to 4-membered spirocycloalkyl ring;

R$_{1a}$ and R$_{1b}$ along with the carbon atoms to which they are attached, can form a 3- to 4-membered cycloalkyl ring;

R$_{1b}$ and R$_{1c}$ along with the carbon atoms to which they are attached, can form a 3- to 4-membered cycloalkyl ring;

R$_2$ is H, halo, C$_{1-3}$ alkyl, or C$_{3-6}$ cycloalkyl;

R$_3$ is C$_{1-4}$ alkoxy, C$_{1-4}$ fluoroalkoxy, or C$_{3-6}$ cycloalkoxy;

R$_4$ is H, halo, C$_{1-4}$ alkyl, C$_{1-4}$ fluoroalkyl, or C$_{3-6}$ cycloalkyl; and R$_5$ is H, halo, C$_{1-4}$ alkyl, C$_{1-4}$ fluoroalkyl, or C$_{3-6}$ cycloalkyl.

2. The compound according to claim 1 or a salt thereof, wherein:

each R$_{1a}$ is independently H, —OH, F, C$_{1-3}$ alkyl, C$_{1-2}$ fluoroalkyl, C$_{1-2}$ alkoxy, C$_{1-2}$ fluoroalkoxy, or C$_{3-6}$ cycloalkyl; or two R$_{1a}$ along with the carbon atom to which they are attached, can form a 3-to 4-membered spirocycloalkyl ring;

each R$_{1b}$ is independently H, —OH, F, C$_{1-2}$ alkyl, C$_{1-2}$ fluoroalkyl, C$_{1-2}$ alkoxy, C$_{1-2}$ fluoroalkoxy, or C$_{3-6}$ cycloalkyl; or two R$_{1b}$ along with the carbon atom to which they are attached, can form a 3- to 4-membered spirocycloalkyl ring;

each R$_{1c}$ is independently H, F, C$_{1-2}$ alkyl, C$_{1-2}$ fluoroalkyl, or C$_{3-6}$ cycloalkyl; or two R$_{1c}$ along with the carbon atom to which they are attached, can form a 3- to 4-membered spirocycloalkyl ring;

R$_2$ is H, F, Cl, C$_{1-2}$ alkyl, or C$_{3-6}$ cycloalkyl;

R$_3$ is C$_{1-3}$ alkoxy, C$_{1-2}$ fluoroalkoxy, or C$_{3-6}$ cycloalkoxy;

R$_4$ is H, halo, C$_{1-4}$ alkyl, C$_{1-4}$ fluoroalkyl, or C$_{3-6}$ cycloalkyl; and R₅ is H, halo, $C_{1-4}$ alkyl, $C_{1-4}$ fluoroalkyl, or $C_{3-6}$ cycloalkyl.

3. The compound according to claim 1 any one of claims 1 to 2 or a salt or thereof, wherein:
X is CH;
Y is N;
each $R_{1a}$ is independently H or $C_{1-2}$ alkyl;
each $R_{1b}$ is independently H, F, —CH₃, —CHF₂, or cyclopropyl; or two $R_{1b}$ along with the carbon atom to which they are attached, can form a 3-membered spirocycloalkyl ring;
each $R_{1c}$ is H;
$R_2$ is H or —CH₃;
$R_3$ is —OCH₃, —OCH(CH₃)₂, or —O(cyclopropyl);
$R_4$ is H; and
$R_5$ is H.

4. The compound according to claim 1 or a salt thereof, wherein:
$R_1$ is:

5. The compound according to claim 1 or a salt thereof, wherein:
each $R_{1a}$ is independently H or $C_{1-2}$ alkyl; and
each $R_{1b}$ is independently H, F, —CH₃, —CHF₂, or cyclopropyl; or two $R_{1b}$ along with the carbon atom to which they are attached form a 3-membered spirocycloalkyl ring.

6. The compound according to claim 1 or a salt thereof, wherein:
R₁ is

7. The compound according to claim 1 or a salt or prodrug thereof, wherein:
each $R_{1a}$ is independently H or $C_{1-2}$ alkyl;
each $R_{1b}$ is independently H, F, —CH₃, —CHF₂, or cyclopropyl; and
each $R_{1c}$ is H.

8. The compound according to claim 1 or a salt thereof, wherein said compound is selected from: 3-(((2S,3S)-3-ethyl-4,4-difluoro-5-oxopyrrolidin-2-yl)methoxy)-5-methoxythieno[3,2-b]pyridine-6-carboxamide (1); 3-(((2S,3S,4S)-3-ethyl-4-fluoro-5-oxopyrrolidin-2-yl)methoxy)-5-methoxythieno[3,2-b]pyridine-6-carboxamide (2); (S)-5-methoxy-3-((5-oxopyrrolidin-2-yl)methoxy)thieno[2,3-b]pyridine-6-carboxamide (3); 3-(((2S,3S,4S)-3-ethyl-4-fluoro-5-oxopyrrolidin-2-yl)methoxy)-5-methoxybenzo[b]thiophene-6-carboxamide (4); (S)-5-methoxy-3-((5-oxopyrrolidin-2-yl)methoxy)thieno[3,2-b]pyridine-6-carboxamide (5); 3-(((2S,3R)-3-ethyl-5-oxopyrrolidin-2-yl)methoxy)-5-methoxythieno[3,2-b]pyridine-6-carboxamide (6); 5-methoxy-3-((5-oxomorpholin-3-yl)methoxy)thieno[3,2-b]pyridine-6-carboxamide (7); 3-(((2 S,3 S,4R)-3-ethyl-4-fluoro-5-oxopyrrolidin-2-yl)methoxy)-5-methoxythieno[3,2-b]pyridine-6-carboxamide (8); 3-(((6S,7R)-7-ethyl-4-oxo-5-azaspiro[2.4]heptan-6-yl)methoxy)-5-methoxythieno[3,2-b]pyridine-6-carboxamide (9); 3,2-b (2S,3R)-3-ethyl-4,4-dimethyl-5-oxopyrrolidin-2-yl) methoxy)-5-methoxythieno[3,2-b]pyridine-6-carboxamide (10); 3-(((2S,4R)-4-fluoro-5-oxopyrrolidin-2-yl)methoxy)-5-methoxythieno[3,2-b]pyridine-6-carboxamide (11); 3-(((2S,3R)-3-(difluoromethyl)-5-oxopyrrolidin-2-yl)methoxy)-5-methoxythieno[3,2-b]pyridine-6-carboxamide (12); 5-methoxy-3,2-b (2S)-4-methyl-5-oxopyrrolidin-2-yl) methoxy)thieno[3,2-b]pyridine-6-carboxamide (13-14); 3-(((2S)-4-ethyl-5-oxopyrrolidin-2-yl)methoxy)-5-methoxythieno[3,2-b]pyridine-6-carboxamide (15-16); 5-methoxy-3-(((2S,3R)-3-methyl-5-oxopyrrolidin-2-yl) methoxy)thieno[3,2-b]pyridine-6-carboxamide (17); 3-(((2S,3S,4R)-3-cyclopropyl-4-fluoro-5-oxopyrrolidin-2-yl)methoxy)-5-methoxythieno[3,2-b]pyridine-6-carboxamide (18); 3,2-b (2S,3R)-3-ethyl-5-oxopyrrolidin-2-yl) methoxy)-5-methoxy-2-methylthieno[3,2-b]pyridine-6-carboxamide (19); 5-cyclopropoxy-3,2-b (2S,3R)-3-ethyl-5-oxopyrrolidin-2-yl)methoxy)thieno[3,2-b]pyridine-6-carboxamide (20); 3-(((2S,3S)-4,4-difluoro-3-methyl-5-oxopyrrolidin-2-yl)methoxy)-5-methoxythieno[3,2-b]pyridine-6-carboxamide (21); 3-(((2 S,3 S,4 S)-3-ethyl-4-fluoro-5-oxopyrrolidin-2-yl)methoxy)-5-methoxy-2-methylthieno[3,2-b]pyridine-6-carboxamide (22); 3-(((2S,3S,4S)-3-ethyl-4-fluoro-5-oxopyrrolidin-2-yl)methoxy)-5-isopropoxythieno [3,2-b]pyridine-6-carboxamide (23); 5-cyclopropoxy-3,2-b (2S,3S,4S)-3-ethyl-4-fluoro-5-oxopyrrolidin-2-yl)methoxy)thieno[3,2-b]pyridine-6-carboxamide (24); (S)-5-methoxy-2-methyl-3,2-b,5-oxopyrrolidin-2-yl)methoxy)thieno[3,2-b]pyridine-6-carboxamide (25); 3,2-b (4R,5S)-5-ethyl-2-oxooxazolidin-4-yl)methoxy)-5-methoxythieno[3,2-b]pyridine-6-carboxamide (26); 3-(((2 S,3S,4R)-4-fluoro-3-methyl-5-oxopyrrolidin-2-yl) methoxy)-5-methoxythieno[3,2-b]pyridine-6-carboxamide (27); 3,2-b (2S,3S,4S)-4-fluoro-3-methyl-5-oxopyrrolidin-2-yl)methoxy)-5-methoxythieno[3,2-b]pyridine-6-carboxamide (28); and 3,2-b (2S,3R)-3-ethyl-5-oxopyrrolidin-2-yl)methoxy)-5-methoxybenzo[b]thiophene-6-carboxamide (29).

9. A pharmaceutical composition comprising one or more compounds according to claim 1 and a pharmaceutically acceptable carrier or diluent.

10. A compound having the structure:

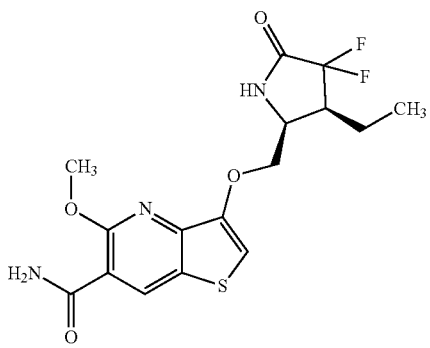 [SMILES: CC[C@H]1[C@@H](COc2csc3cc(C(N)=O)c(OC)nc23)NC(=O)C1(F)F]

or a salt thereof.

11. The compound according to claim 10.

12. The compound according to claim 10, wherein said compound is a salt.

13. A pharmaceutical composition comprising a compound according to claim 10 or a pharmaceutically-acceptable salt thereof and a pharmaceutically acceptable carrier.

14. A compound having the structure:

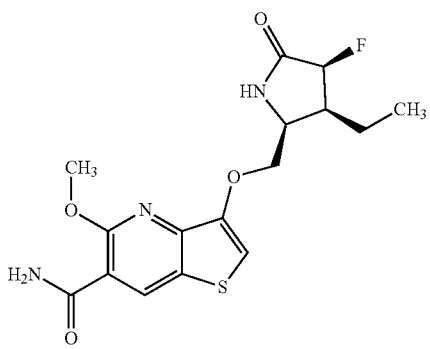 [SMILES: CC[C@@H]1[C@H](F)C(=O)N[C@@H]1COc1csc2cc(C(N)=O)c(OC)nc12]

or a salt thereof.

15. The compound according to claim 14.

16. The compound according to claim 14, wherein said compound is a salt.

17. A pharmaceutical composition comprising a compound according to claim 14 or a pharmaceutically-acceptable salt thereof and a pharmaceutically acceptable carrier.

18. A compound having the structure:

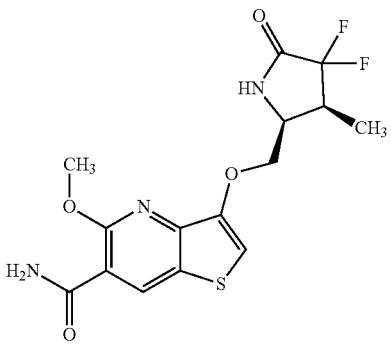 [SMILES: COc1nc2c(OC[C@H]3NC(=O)C(F)(F)[C@H]3C)csc2cc1C(N)=O]

or a salt thereof.

19. The compound according to claim 18.

20. The compound according to claim 18, wherein said compound is a salt.

21. A pharmaceutical composition comprising a compound according to claim 18 or a pharmaceutically-acceptable salt thereof and a pharmaceutically acceptable carrier.

* * * * *

UNITED STATES PATENT AND TRADEMARK OFFICE
CERTIFICATE OF CORRECTION

PATENT NO. : 10,829,496 B2
APPLICATION NO. : 16/612478
DATED : November 10, 2020
INVENTOR(S) : Saleem Ahmad et al.

It is certified that error appears in the above-identified patent and that said Letters Patent is hereby corrected as shown below:

In the Claims

In Claim 1, Column 54, Line 31, delete "3-to" and insert -- 3- to --, therefor.

In Claim 2, Column 54, Line 53, delete "3-to" and insert -- 3- to --, therefor.

In Claim 3, Column 55, Line 3-4, after "claim 1" delete "any one of claims 1 to 2".

In Claim 3, Column 55, Line 4, after "salt" delete "or".

In Claim 6, Column 55, Line 38, delete "Ri" and insert -- $R_1$ --, therefor.

In Claim 8, Column 56, Line 3, delete "oxopyrrolidin -2" and insert -- oxopyrrolidin-2 --, therefor.

In Claim 8, Column 56, Line 15, delete "(((2 S,3 S,4R)" and insert -- (((2S,3S,4R) --, therefor.

In Claim 8, Column 56, Line 20, delete "3,2-b (2S,3R)" and insert -- 3-(((2S,3R) --, therefor.

In Claim 8, Column 56, Line 28, delete "-3,2-b (2S)" and insert -- -3-(((2S) --, therefor.

In Claim 8, Column 56, Line 37, delete "3,2-b (2S,3R)" and insert -- 3-(((2S,3R) --, therefor.

In Claim 8, Column 56, Line 39 (Approx.), delete "-3,2-b (2S,3R)" and insert -- -3-(((2S,3R) --, therefor.

In Claim 8, Column 56, Line 44, delete "(((2 S,3 S,4 S)" and insert -- (((2S,3S,4S) --, therefor.

In Claim 8, Column 56, Line 46, delete "[3 ,2-b]" and insert -- [3,2-b] --, therefor.

In Claim 8, Column 56, Line 50, delete "-3,2-b (2S,3S,4S)" and insert -- -3-(((2S,3S,4S) --, therefor.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,829,496 B2

In Claim 8, Column 56, Line 52, delete "-3,2-b,5-" and insert -- -3-((5- --, therefor.

In Claim 8, Column 56, Line 54 (Approx.), delete "3,2-b (4R,5S)" and insert -- 3-(((4R,5S) --, therefor.

In Claim 8, Column 56, Line 57 (Approx.), delete "3 -methyl" and insert -- 3-methyl --, therefor.

In Claim 8, Column 56, Line 59 (Approx.), delete "3,2-b (2S,3S,4S)" and insert -- 3-(((2S,3S,4S) --, therefor.

In Claim 8, Column 56, Line 61 (Approx.), delete "3,2-b (2S,3R)" and insert -- 3-(((2S,3R) --, therefor.